(12) United States Patent
Govil et al.

(10) Patent No.: US 10,357,594 B2
(45) Date of Patent: Jul. 23, 2019

(54) SOLUBLE BONE MARROW PROTEIN COMPOSITIONS, METHODS OF MAKING, AND USES THEREOF

(71) Applicant: Biologica Technologies, Carlsbad, CA (US)

(72) Inventors: Amit Prakash Govil, Carlsbad, CA (US); Bryan Choi, Carlsbad, CA (US); Sahil Jalota, Carlsbad, CA (US)

(73) Assignee: Biologica Technologies, Carlsbad, CA (US)

( * ) Notice: Subject to any disclaimer, the term of this patent is extended or adjusted under 35 U.S.C. 154(b) by 0 days.

(21) Appl. No.: 15/525,418

(22) PCT Filed: Oct. 12, 2016

(86) PCT No.: PCT/US2016/056617
§ 371 (c)(1),
(2) Date: May 9, 2017

(87) PCT Pub. No.: WO2017/066306
PCT Pub. Date: Apr. 20, 2017

(65) Prior Publication Data
US 2018/0200406 A1 Jul. 19, 2018

Related U.S. Application Data

(60) Provisional application No. 62/240,318, filed on Oct. 12, 2015, provisional application No. 62/240,348, filed on Oct. 12, 2015.

(51) Int. Cl.
*A61L 27/38* (2006.01)
*A61K 38/18* (2006.01)
*A61L 27/36* (2006.01)
*A61L 27/54* (2006.01)
*A61K 38/01* (2006.01)

(52) U.S. Cl.
CPC .......... *A61L 27/3834* (2013.01); *A61K 38/01* (2013.01); *A61K 38/18* (2013.01); *A61L 27/3604* (2013.01); *A61L 27/3608* (2013.01); *A61L 27/3683* (2013.01); *A61L 27/3895* (2013.01); *A61L 27/54* (2013.01); *A61L 2300/414* (2013.01); *A61L 2430/02* (2013.01); *A61L 2430/38* (2013.01)

(58) Field of Classification Search
None
See application file for complete search history.

(56) References Cited

U.S. PATENT DOCUMENTS

2010/0152863 A1 6/2010 Govil

FOREIGN PATENT DOCUMENTS

WO 2014/151019 A2 9/2014

OTHER PUBLICATIONS

Yang, Bin; et al; "Characterization of Bioactive Recombinant Human Lysozyme Expressed in Milk of Cloned Transgenic Cattle" PLoS One, 6, e17593, 2011 (Year: 2011).*
International Search Report for PCT/US2016/056617 dated Feb. 21, 2017.

* cited by examiner

*Primary Examiner* — David W Berke-Schlessel
(74) *Attorney, Agent, or Firm* — Thomas | Horstemeyer, LLP.

(57) ABSTRACT

Provided herein are soluble bioactive factor solutions, grafting scaffolds containing the bioactive factor solutions, and methods of making and using the same.

19 Claims, 20 Drawing Sheets

SOLUBLE BONE MARROW PROTEIN COMPOSITIONS, METHODS OF MAKING, AND USES THEREOF

CROSS-REFERENCE TO RELATED APPLICATIONS

This application is the 35 U.S.C. § 371 national stage application of PCT Application No. PCT/US2016/056617, filed on Oct. 12, 2016, where the PCT also claims the benefit of and priority to U.S. Provisional Patent Application No. 62/240,318, filed on Oct. 12, 2015, entitled "SOLUBLE BONE MARROW PROTEIN COMPOSITIONS, METHODS OF MAKING, AND USES THEREOF," and U.S. Provisional Patent Application No. 62/240,348, filed on Oct. 12, 2015, entitled "SCAFFOLD MATERIALS CONTAINING SOLUBLE BONE MARROW PROTEIN COMPOSITIONS, METHODS OF MAKING, AND USES THEREOF," the contents of which are incorporated by reference herein in their entirety.

BACKGROUND

Bone and tissue grafting are surgical procedures that replace missing bone or other tissues to repair bone and other joint or other tissue damage. Generally, bone has the ability to regenerate completely but typically need some sort of scaffold to do so. Current bone grafts can be natural (allograft or autologous) or synthetic compositions that have similar mechanical properties as bone (e.g. hydroxyapatite). Despite the regenerative nature of bone, conditions are not always ideal for healing of the bone graft. Indeed, despite the efficacy of modern internal fixation techniques, infection, poor vascularity, malnutrition, and substantial bone or soft tissue loss can impede effective osteogenesis. As such there exists a need for improved compositions and methods for increasing the healing efficacy of existing bone and tissue grafting techniques.

SUMMARY

Provided herein are methods of making a soluble bone marrow protein composition, that can contain the steps of harvesting bone marrow from a donor to obtain harvested bone marrow, where the bone marrow contains bone marrow cells, heating the harvested bone marrow to at least 20° C., lysing bone marrow cells to obtain a bone marrow cell lysate; and dehydrating the soluble bone marrow protein fraction to obtain a dehydrated soluble bone marrow protein composition. The method can further contain the optional step of fractionating the bone marrow cell lysate via centrifugation to obtain a soluble bone marrow protein fraction after performing the step of lysing bone marrow cells to obtain a bone marrow cell lysate. The step of heating the harvested bone marrow can occur at about 20° C. to about 40° C. The method can also include the step of washing the harvested bone marrow. In some embodiments, the step of washing the harvested bone marrow, heating the harvested bone marrow, and lysing bone marrow cell can occur simultaneously. The method can also include the step of adding a stabilization solution prior to dehydrating. The method can also include the optional step of filtering the soluble bone marrow protein fraction. In some embodiments, the filtering can remove at least nucleic acids from the soluble bone marrow protein fraction. The method can further include the step of selectively filtering the bone marrow cells to obtain a desired cell population prior to or during the step of lysing the bone marrow cells. The step of lysing can further include lysing the desired cell population. The desired cell population can be mesenchymal stem cells. The method can further include the step of wherein an amount of the dehydrated soluble bone marrow protein composition is implanted in or otherwise administered to a subject in need thereof. In some embodiments, the dehydrated soluble bone marrow protein composition in stabilization solution is implanted in or otherwise administered to a subject in need thereof. The method can further include the step of applying an amount of the dehydrated soluble bone marrow protein composition to a scaffold. In some embodiments, the scaffold is implanted in or otherwise administered to a subject in need thereof. The method can further include the step of applying an amount of the dehydrated soluble bone marrow protein composition in stabilization solution to a scaffold. The scaffold can be implanted in or otherwise administered to a subject in need thereof.

Also provided herein are soluble bone marrow protein compositions that can contain a bioactive factor, where the soluble bone marrow protein composition is made by a method that can include the steps of harvesting bone marrow from a donor to obtain harvested bone marrow, where the bone marrow contains bone marrow cells, heating the harvested bone marrow to at least 20° C., lysing bone marrow cells to obtain a bone marrow cell lysate; and dehydrating the soluble bone marrow protein fraction to obtain a dehydrated soluble bone marrow protein composition. The bioactive factor can be a protein selected from the group of: a bone morphogenetic protein; epidermal growth factor, an insulin-like growth factor, a fibroblast growth factor, vascular endothelial growth factor, oteoprotegerin, and osteopontin. The bioactive factor can be present in the soluble bone marrow protein composition at a concentration of about 0 µg/g to about 100 mg/g. The bioactive factor can be bone morphogenetic protein 2 and can be present at a concentration of at least 1 pg/g. The bioactive factor can be acidic fibroblast growth factor and can be present at a concentration of at least 1 pg/g. The bioactive factor can be basic fibroblast growth factor and can be present at a concentration of at least 1 pg/g. The bioactive factor can be vascular endothelial growth factor and can be present at a concentration of at least 1 pg/g.

Also provided herein are methods of treating a subject in need thereof that can include the step of implanting or administering a soluble bone marrow protein composition, where the protein composition can include a bioactive factor, where the soluble bone marrow protein composition is made by a method that can include the steps of harvesting bone marrow from a donor to obtain harvested bone marrow, where the bone marrow contains bone marrow cells, heating the harvested bone marrow to at least 20° C., lysing bone marrow cells to obtain a bone marrow cell lysate; and dehydrating the soluble bone marrow protein fraction to obtain a dehydrated soluble bone marrow protein composition. The subject in need thereof can have a bone fracture. The subject in need thereof can need a bone fusion. The subject in need thereof can be in need of a spinal fusion.

Also provided herein are implants that can contain an amount of a scaffold and a non-recombinant soluble bone marrow protein composition, where the non-recombinant bone marrow protein composition can contain a bioactive factor and an acid. The scaffold can be in the form of a block, chips, morsels, canister, foam, cement, or bioactive foam. The bioactive factor can be present in the non-recombinant soluble bone marrow protein composition at a concentration of at least at least 1 pg/g. The bioactive factor can be present in the non-recombinant soluble bone marrow protein composition at a concentration of about 0 µg/g to about 100 mg/g. The bioactive factor can be selected from the following group of: a bone morphogenetic protein, an epidermal growth factor, an insulin-like growth factor, a fibroblast growth factor, vascular endothelial growth factor, osteoprotegerin, and osteopontin, and combinations thereof. The bioactive factor can be bone morphogenetic protein 2. The bone morphogenetic protein can be present at a concentration of at least 1 pg/g. The bioactive factor can be insulin like growth factor-1. The bioactive factor can be α-fibroblast growth factor and can be present at a concentration of at least 1 pg/g. The bioactive factor can be β-fibroblast growth factor. The β-fibroblast growth factor can be present at a concentration of at least 1 pg/g. The bioactive factor can be vascular endothelial growth factor. The vascular endothelial growth factor can be present at a concentration of at least 1 pg/g. The non-recombinant soluble bone marrow protein composition can be 90% to 100% dehydrated. The scaffold material can be VITOSS® material or CORTOSS® material. The scaffold material can be a biopolymer, bone, decellularized bone, extracellular matrix or components thereof, fibrin collagen, chitosan, alginate, calcium phosphate, calcium sulfate, poly(alpha-hydroxy acids) such as poly(lactic-co-glycolic acid) and polyglycolic acid, CUPE polymer, polyethylene glycol, or any combinations thereof.

Also provided herein are methods that can contain the step of implanting in or administering to a subject in need thereof an implant that can contain an amount of a scaffold and a non-recombinant soluble bone marrow protein composition, where the non-recombinant bone marrow protein composition can contain a bioactive factor and an acid. The subject in need thereof can be in need of a bone graft or a bone fusion.

Also provided herein are methods that can include the step of implanting or administering an implant that can contain an amount of a scaffold and a non-recombinant soluble bone marrow protein composition, where the non-recombinant bone marrow protein composition can contain a bioactive factor and an acid, where the subject in need thereof can have a bone fracture, diseased bone, joint fracture, a diseased joint, or a combination thereof.

Also provided herein are methods of fusing a portion of a spine, where the method can contain the step of implanting or administering an implant that can contain an amount of a scaffold and a non-recombinant soluble bone marrow protein composition, where the non-recombinant bone marrow protein composition can contain a bioactive factor and an acid.

Also provided herein are methods of grafting bone where the method can contain the step of implanting or administering an implant that can contain an amount of a scaffold and a non-recombinant soluble bone marrow protein composition, where the non-recombinant bone marrow protein composition can contain a bioactive factor and an acid.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
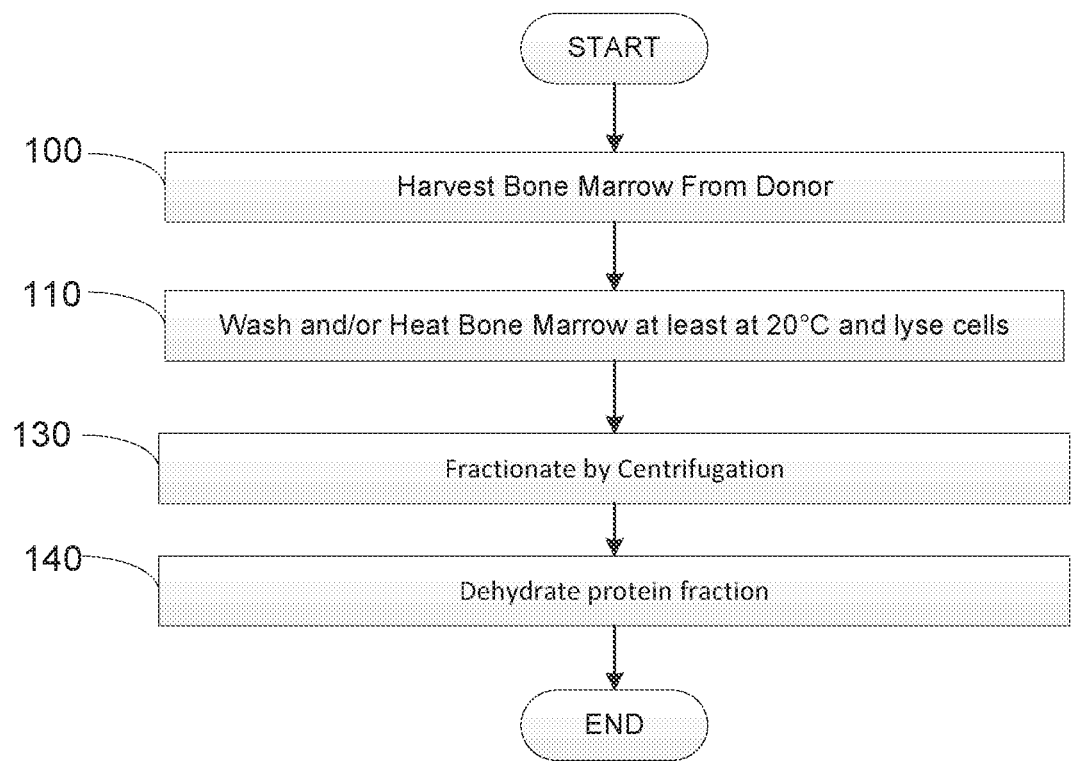
FIG. 1 is a flow diagram showing one embodiment of a method to produce soluble bone marrow derived proteins.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited unless expressly stated otherwise. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "adipocyte" refers to a cell type also known as a lipocyte or fat cell. Adipocytes are the cells that primarily compose adipose tissue, specialized in storing energy as fat.

As used herein, "additive effect" refers to an effect arising between two or more molecules, compounds, substances, factors, or compositions that is equal to or the same as the sum of their individual effects.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "allogeneic" refers to involving, derived from, or being individuals of the same species that are sufficiently genetically different so as to interact with one another antigenicaly.

As used herein, "allograft" refers to a graft that is derived from one member of a species and grafted in a genetically dissimilar member of the same species.

As used herein, "autograft" refers to a graft that is derived from a subject and grafted into the same subject from which the graft was derived.

As used herein, "autologous" refers to being derived from the same subject that is the recipient.

As used herein, "bioactive" refers to the ability or characteristic of a material, compound, molecule, or other particle that interacts with or causes an effect on any cell, tissue and/or other biological pathway in a subject.

As used herein, "bioactive factor" refers to a compound, molecule, or other particle that interacts with or causes an effect on any cell, tissue, and/or other biological pathway in a subject.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "cell," "cell line," and "cell culture" include progeny. It is also understood that all progeny may not be precisely identical in DNA content, due to deliberate or inadvertent mutations. Variant progeny that have the same function or biological property, as screened for in the originally transformed cell, are included.

As used herein, "complete extracellular matrix" refers to extracellular matrix that has all components (proteins, peptides, proteoglycans, and the like) present and may or may not include other cells that are embedded in the extra cellular matrix.

As used herein, "concentrated" used in reference to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "control" is an alternative subject or sample used in an experiment for comparison purposes and included to minimize or distinguish the effect of variables other than an independent variable.

As used herein, "culturing" refers to maintaining cells under conditions in which they can proliferate and avoid senescence as a group of cells. "Culturing" can also include conditions in which the cells also or alternatively differentiate.

As used herein, "decellularized extracellular matrix" refers to complete extracellular matrix that has been processed to remove any cells embedded within the extracellular matrix.

As used herein, "diluted" used in reference to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "donor" refers to a subject from which cells or tissues are derived.

As used herein, "effective amount" can refer to an amount sufficient to effect beneficial or desired results. An effective amount can be administered in one or more administrations, applications, or dosages.

As used herein, "endogenous" refers to a compound, substance, or molecule originating from within a subject or donor, including their cells or tissues.

As used herein, "extra cellular matrix" refers to the non-cellular component surrounding cells that provides support functions to the cell including structural, biochemical, and biophysical support, including but not limited to, providing nutrients, scaffolding for structural support, and sending or responding to biological cues for cellular processes such as growth, differentiation, and homeostasis.

As used herein, "extracellular matrix component" refers to a particular component. By way of a non-limiting example, an extracellular matrix compartment can be a specific class of comments (e.g. proteoglycans) or individual component (e.g. collagen I) that is separated or isolated from the other extracellular components. These components can be made synthetically.

As used herein, "exogenous" refers to a compound, substance, or molecule coming from outside a subject or donor, including their cells and tissues.

As used herein, "filler" refers to a substance used to fill a cavity or depression. The filler can fill the depression such that it is level with the surrounding area or that the cavity is filled, such that the depth of the depression or volume of the cavity is decreased, or such that the area that was the depression is now raised relative to the areas immediately surrounding the depression.

As used herein "hydrogel" refers to a network of hydrophilic polymer chains that are dispersed in water. "Hydrogel" also includes a network of hydrophilic polymer chains dispersed in water that are found as a colloidal gel.

As use herein, "immunogenic" or "immunogenicity" refers to the ability of a substance, compound, molecule, and the like (referred to as an "antigen") to provoke an immune response in a subject.

As used herein, "implant" or "graft," as used interchangeably herein, refers to cells, tissues, or other compounds, including metals and plastics, that are inserted into the body of a subject.

As used herein, "isolated" means separated from constituents, cellular and otherwise, with which the polynucleotide, peptide, polypeptide, protein, antibody, or fragments thereof, are normally associated in nature. A non-naturally occurring polynucleotide, peptide, polypeptide, protein, antibody, or fragments thereof, does not require "isolation" to distinguish it from its naturally occurring counterpart.

As used herein, "negative control" refers to a "control" that is designed to produce no effect or result, provided that all reagents are functioning properly and that the experiment is properly conducted. Other terms that are interchangeable with "negative control" include "sham," "placebo," and "mock."

As used herein, "physiological solution" refers to a solution that is about isotonic with tissue fluids, blood, or cells.

As used herein, "positive control" refers to a "control" that is designed to produce the desired result, provided that all reagents are functioning properly and that the experiment is properly conducted.

As used herein, "preventative" refers to hindering or stopping a disease or condition before it occurs or while the disease or condition is still in the sub-clinical phase.

As used herein "scaffold" can refer to any suitable material to which the compounds provided herein can be bound to, adsorbed to, or otherwise attached to, including but not limited to, the graft materials described in described in U.S. Pat. Nos. 5,681,872; 5,914,356; 5,939,039; 6,325,987; 6,383,519; 6,521,246; 6,736,799; 6,800,245; 6,969,501; 6,991,803; 7,052,517; 7,189,263; 7,534,451; 8,303,967; 8,460,686; 8,647,614, which are incorporated by reference herein as if expressed in their entirety, such as but not limited to, VITOSS® and CORTOSS® material.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "therapeutic" refers to treating or curing a disease or condition.

As used herein "self-assembling peptides" refer to peptides which undergo spontaneous assembly into ordered nanostructures. "Self-assembling peptides" include di-peptides, lego peptides, surfactant peptides, molecular paint or carpet peptides, and cyclic peptides.

As used herein, "specific binding" refers to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, "syngeneic" refers to subjects or donors that are genetically similar enough so as to be immunologically compatible to allow for transplantation, grafting, or implantation.

As used herein, "synergistic effect," "synergism," or "synergy" refers to an effect arising between two or more molecules, compounds, substances, factors, or compositions that is greater than or different from the sum of their individual effects.

As used herein "xenograft" or "xenogeneic" refers to a substance or graft that is derived from one member of a species and grafted or used in a member of a different species.

Discussion

Bone grafting is a common procedure performed for a variety of orthopedic and dental reasons. Many materials have been developed that can be used for bone graft procedures. Such materials include, but are not limited to, autograft, allograft, and synthetic bone graft materials. While these materials have enjoyed a certain amount of clinical success, donor morbidity when using autograft materials, adverse recipient immune response when using allograft materials, and limited bone remodeling and low osteoconductivity that can be observed when using synthetic materials. Attempts to improve the clinical performance of all types of materials have employed the use of recombinant or synthetic bioactive factors that are involved in the bone-remodeling process. While there have been attempts to obtain bioactive factors directly from various tissue sources, all have relied upon harsh chemicals to isolate the bioactive factors, which can lead to low yields of viable bioactive factors such and reduce clinical performance of the bioactive factors obtained. Further, the variability in the amount and type of bioactive factors obtained directly from tissue sources due to the methods used to obtain the bioactive factors severely limits this approach for any practical clinical purpose.

With the aforementioned shortcomings in mind, described herein are soluble bone marrow protein compositions and scaffolds that can include a soluble bone marrow protein composition provided herein. The soluble bone marrow protein composition can be a non-recombinant soluble bone marrow protein composition. The soluble bone marrow protein compositions provided herein can, in some embodiments, overcome one or more of the shortcomings of existing soluble bone marrow compositions and graft scaffold materials. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Soluble Bone Marrow Protein Compositions and Scaffolds

Soluble Bone Marrow Protein Compositions

Bone marrow is the soft, spongey, gelatinous tissue found in the hollow spaces in the interior of bones. Bone marrow contains stem cells that are supported by a fibrous tissue called the stroma. There are two main types of stem cells in bone marrow: (1) hematopoietic stem cells and (2) bone marrow mesenchymal stem cells (bmMSCs). bmMSCs can differentiate into a variety of cells types including without limitation, fibroblasts, chondrocytes, osteocytes, myotubes, stromal cells, adipocytes, astrocytes, and dermal cells. In addition to bmMSCs, bone marrow stroma contains other types of cells including fibroblasts (reticular connective tissue) macrophages, adipocytes, osteoblasts, osteoclasts, red blood cells, white blood cells, leukocytes, granulocytes, platelets, and endothelial cells.

The soluble bone marrow protein compositions can contain proteins and/or other non-recombinant bioactive factors derived from bone marrow mesenchymal stem cells, fibroblasts, chondrocytes, osteocytes, red blood cells, white blood cells, leukocytes, granulocytes, platelets, and/or osteoclasts. The proteins can be intracellular proteins or membrane associated proteins. Such proteins include without limitation, bone morphogenetic proteins (BMPs) (e.g. BMP-1, BMP-2, BMP-3, BMP-4, BMP-5, BMP-7 and BMP-8a), transforming growth factors (TGF-β1, TGF-β2), epidermal growth factor (EGF), hepatocyte growth factor (HGF), insulin-like growth factors (IGFs) (e.g. IGF-1), fibroblast growth factors (FGFs) (e.g. aFGF (acidic fibroblast growth factor) and bFGF (basic fibroblast growth factor)), vascular endothelial growth factor (VEGF), platelet derived growth factor—BB (PDGF-BB), osteoprotegerin (OPG), and osteopontin (OPN).

The soluble bone marrow protein composition can be 0% to 100% dehydrated. In some embodiments the soluble bone marrow protein composition can be about 100% dehydrated. In some embodiments, the soluble bone marrow protein composition can be liquid or flowable solution. In some embodiments, the soluble bone marrow protein composition is frozen. Techniques for freezing include slow and flash freezing in liquid nitrogen. The soluble bone marrow protein composition can be frozen to less than about 0° C. such as −10, −20, and −80° C. or more. The soluble bone marrow protein compositions do not inherently contain recombinant proteins. The concentration of one or more of the bioactive factors in the soluble bone marrow protein compositions can be present in the composition at a concentration greater than or less than would be found in a cell within the body. The soluble bone marrow protein composition(s) as described herein can increase the efficiency of implant and/or graft integration and/or healing over that of the proteins if present in the context of complete bone marrow or other complete bodily fluid or tissue.

Additionally, the soluble bone marrow protein composition(s) described herein can lack the immunogenic proteins and other components that are present in complete bone marrow and/or other complete bodily fluid or tissue. The soluble bone marrow protein compositions provided herein, in some embodiments, do not include a recombinant or synthetic protein or other bioactive factor. In other words, in some embodiments the soluble bone marrow protein composition can be a non-recombinant soluble bone marrow protein composition.

Any given bone marrow protein and/or other bioactive factor can be present in the soluble bone marrow protein composition at a concentration of 0 μg/g to about 100 mg/g of isolated protein in the final product, dehydrated or otherwise provided. The soluble bone marrow protein composition can include at least 1 pg/g, about 1 pg/g to about 100 μg/g, about 7 μg/g to about 100 μg/g, or about 7 μg/g to about 35 μg/g BMP-2 protein derived directly from bone marrow. The soluble bone marrow protein composition can include at least about 1 pg/g aFGF, about 1 pg/g to about 100 μg/g aFGF, about 1 ng/g to about 100 ng/g aFGF, or about 20 to about 40 ng/g aFGF. The soluble bone marrow protein composition can include at least about 1 pg/g bFGF, about 1 pg/g to about 100 μg/g bFGF, about 1 ng/g to about 100 ng/g bFGF, or about 20 ng/g to about 40 ng/g bFGF. The concentration of VEGF in the soluble bone marrow protein composition can be at least about 1 pg/g, or about 1 pg/g to about 100 μg/g VEGF, about 1 ng/g to about 150 ng/g VEGF, or about 60 ng/g to about 90 ng/g VEGF. The soluble bone marrow protein composition can include at least 1 pg/g PDGF, or about 1 pg/g PDGF to about 100 μg/g PDGF, about 500 pg/g to about 500 ng/g PDGF, about 900 pg/g to about 100 ng/g PDGF, or to about 950 pg/g to about 50 ng/g PDGF. The soluble bone marrow protein composition can include at least 1 pg/g OPN, or about 1 pg/g OPN to about 100 μg/g OPN, about 500 pg/g OPN to about 500 ng/g OPN, about 900 pg/g to about 100 ng/g OPN, or to about 950 pg/g to about 50 ng/g OPN.

Additionally, the soluble bone marrow protein composition can also contain an amount of a suitable acid. In some embodiments, the acid is a residual or other amount of the acid that can be used to lyse the bone marrow cells. In some embodiments, the acid can be glutamic acid or acetic acid. Other suitable acids are described elsewhere herein. The acid can facilitate and/or increase binding of the proteins in the soluble protein composition to a scaffold when the proteins are diluted or rehydrated during use, which is described elsewhere herein.

In some embodiments, soluble bone marrow protein composition can include a stabilizer composition or stabilizer compounds. Suitable stabilization compositions can include, but are not limited to preservatives, antibiotics, antivirals, antifungals, pH stabilizers, osmostablizers, anti-inflammants, anti-neoplastics, chemotherapeutics, immunomodulators, chemoattractants, growth factors, anticoagulants, or combinations thereof. The stabilization solution can increase shelf life of the soft tissue soluble protein composition and/or reduce denaturation of proteins during dehydration, sterilization, and/or storage. In addition, other materials, such as nitrogen, can be used to help reduce free radical formation and denaturation during sterilization. In some embodiments, the stabilization solution per cc of final product can be about 1 mg Sucrose, 5 mg Glycine, 3.7 mg I-Glutamic Acid, 0.02 mg NaCl and 0.02 mg Polysorbate-80.

In some embodiments, a dehydrated or liquid soluble bone marrow protein composition can be reconstituted. This can result in a dilution of the bioactive factors within the dehydrated soluble bone marrow composition. In some embodiments, dehydration of a liquid soluble bone marrow protein composition can be dehydrated, which can result in a concentration of the proteins in the composition. The soluble bone marrow protein composition can be diluted/concentrated from 0.1 to 100 fold, 0.1 to 50 fold, 0.1 to 20 fold, or 0.1 to 5 fold.

In some embodiments, the final volume of a reconstituted or a liquid soluble bone marrow protein composition can be at least 1 cc, or 1 cc to about 100 cc, about 1 cc to about 50 cc, 1 cc to about 25 cc, about 1 cc to about 20 cc, about 1 cc to about 10 cc. The final soluble bone marrow protein product can be dehydrated or reconstituted to achieve a desired volume or particular protein concentration or composition.

Scaffolds Including a Soluble Bone Marrow Derived Composition

Many suitable graft scaffold materials are known in the art and can include those from autograph, allograft and synthetic sources. CORTOSS® bone augmentation material is a synthetic, injectable, non-resorbable, polymer composite that mimics cortical bone. CORTOSS® bone augmentation material is a self-setting glass ceramic polymeric composite engineered specifically to mimic the characteristics of human bone and can provide fixation for vertebral compression fractures ("VCFs"). Laboratory tests demonstrate that CORTOSS® bone augmentation material can exhibit compressive strength similar to human bone.

VITOSS® bone graft substitute material is a synthetic, ultra-porous resorbable beta-tricalcium phosphate bone void filler that can be used to help the subject's body guide the three-dimensional regeneration of the patient's own bone. VITOSS® bone graft substitute material's ultra-porosity can allow it to soak and hold up to its own volume of other compositions. VITOSS® bone graft substitute material integrates well into existing bone and can allow for bone in-growth and maturation. VITOSS® bone graft substitute material can be provided in a variety of platforms including, but not limited to, blocks, chips, morsels (micro and macro) canisters (micro and standard), foam (strips, cylinders, flow, shapes, and packs), cement (e.g. a bone graft cement) and bioactive foam (strips and packs). VITOSS® foam-based bone graft materials combine the base VITOSS® material technology with resorbable biomaterials to produce a wide array of pliant, flexible, flowable and compression resistant bone graft materials. The cement can exhibit exothermic properties that result in burning of tissues such as nerves in the area surrounding the implant and in some instances improve the clinical outcome and/or recovery of the recipient. The VITOSS® foam-based bone graft materials can soak and hold their own volume in other compositions (e.g. blood and bone marrow aspirate while retaining these biological fluids in pliable and compression resistant forms. These forms can be designed into specific shapes and material characteristics to meet a surgeon's need for handling and delivery in a variety of surgical approaches and applications.

VITOSS® Boactive bone graft substitute materials also contain bioactive glass. Upon implantation, the ionic constituents (e.g. Si+, Na+, $Ca^{2+}$) of bioactive glass can be released into the surrounding environment and can react with bodily fluids. This reaction can produce the deposition of a thin layer of physiologic CaP at its surface. This can attract osteoblasts to the layer to create a matrix that can produce an osteostimulatory effect. This can lead to the bonding of new bone to the scaffold.

As previously discussed, the VITOSS® and CORTOSS® synthetic scaffolds have been described to be supplemented with autologous and allogeneic whole bodily fluids and tissue such as blood and/or bone marrow aspirate. Currently, scaffold materials, including VITOSS® and CORTOSS® synthetic scaffolds, have been combined only with recombinant proteins.

Provided herein are grafting scaffold materials (also referred to herein as "scaffolds") that can include a soluble bone marrow protein composition provided elsewhere herein that can have one or more proteins of the composition bound adsorbed, absorbed, or is otherwise attached to or associated with a scaffold material. Described herein are embodiments of scaffolds, including VITOSS® and CORTOSS® materials, biopolymers, collagen, chitosan, alginate, calcium phosphate, calcium sulfate, or any combinations thereof further containing a soluble bone marrow protein composition described herein.

The soluble bone marrow protein composition can be any soluble bone marrow protein composition provided herein. The soluble bone marrow protein composition including or not including the scaffold material can be a 0% to 100% dehydrated. The soluble bone marrow composition, proteins and/or other bioactive factor(s) can become solubilized and/or reconstituted when contacted with bodily fluids, for example, when the VITOSS® material, CORTOSS® material, and/or other scaffold material containing the soluble bone marrow protein composition are implanted in or otherwise administered to a subject in need thereof. As described elsewhere herein, the soluble bone marrow protein composition can contain an amount of an acid. The acid can be acetic acid, formic acid, trichloroacetic acid, hydrofluoric acid, hydrocyanic acid, hydrogen sulfide, or hydrochloric acid. The acid can be a residual amount left over from the method of producing the soluble bone marrow composition. The acid can facilitate and/or increase the binding and/or retention of the protein(s) and/or other bioactive factors in the soluble bone marrow protein composition bind to or otherwise be attached to or associated with the scaffold material.

Scaffold Materials

The scaffold material can be as described in U.S. Pat. Nos. 5,681,872; 5,914,356; 5,939,039; 6,325,987; 6,383,519; 6,521,246; 6,736,799; 6,800,245; 6,969,501; 6,991,803; 7,052,517; 7,189,263; 7,534,451; 8,303,967; 8,460,686; 8,647,614, which are incorporated by reference herein as if expressed in their entirety. Other suitable scaffold materials include biopolymers, bone, decellularized bone, extracellular matrix or components thereof, fibrin collagen, chitosan, alginate, calcium phosphate, calcium sulfate, poly(alpha-hydroxy acids) such as poly(lactic-co-glycolic acid) and polyglycolic acid, CUPE polymer, polyethylene glycol, or any combinations thereof. The scaffold material can be porous. The scaffold material can be a natural material, synthetic material, or a combination thereof. The scaffold material can be biocompatible, nontoxic, and/or non-inflammatory. The scaffold material can support cell attachment, cell proliferation, extracellular and/or bone matrix production, and/or cell differentiation. The scaffold material can be biodegradable. The scaffold material can be sterilized. Other scaffold materials and attributes will be appreciated by those of skill in the art in view of the discussion provided herein.

Methods of Making the Soluble Bone Marrow Protein Compositions

Described herein are methods for producing compositions containing soluble bone marrow proteins and/or other bioactive factor(s). The methods described herein can also result in a composition containing a dehydrated soluble bone marrow protein(s) and/or other bioactive factor(s). In some embodiments, the dehydrated soluble bone marrow protein(s) and/or other bioactive factor(s) can bind to a scaffold upon reconstitution, or encapsulated prior to delivery, such as when the dehydrated soluble protein composition comes in contact with a bodily fluid, solution containing water, or saline. The soluble protein compositions prepared by the methods described herein can have a greater amount and/or concentration of bone marrow protein(s) and/or additional bioactive factor(s), and/or less immunogenicity than other osteoinductive/osteostimulatory compositions, implants, or devices incorporating complete bone marrow and/or other complete bodily fluids or tissues. The soluble bone marrow protein compositions can contain bioactive proteins such as, but not limited to, BMP-2, acidic-FGF, basic-FGF, IGF, BMP-7, HGF, VEGF, PDGF-BB, OPG, and OPN.

Attention is first directed to FIG. 1, which shows an embodiment of a method of producing a soluble protein composition from bone marrow. The bone marrow can be harvested from a cadaver or from a living subject. The method can begin by harvesting bone marrow from a donor 100. The donor can be a cadaver or can be a living subject. The bone marrow can be autologous, allogeneic or xenogenic. The bone marrow can be harvested in any way generally known in the art. The bone marrow can be obtained from cancellous, corticocancellous, and/or cortical bone. The harvest of the bone marrow may also include bone prior to washing. After the bone marrow has been harvested, the bone marrow is washed 110 in a solution. The wash solution may contain water, saline, antibiotic, antiseptic, antifungal, or crystalloid solution. In some embodiments, the wash solution is only water. Washing can take place at least at 20° C. In some embodiments, washing takes place at about 20° C. to about 37° C. In further embodiments, washing takes place at about 20° C. to about 40° C. In some embodiments, the washing takes place at 37° C. Heating the bone marrow during washing facilitates the reduction in viscosity or removal of undesired fat (adipocytes) from other types of bone marrow cells. The washing/heating step can be performed under physical agitation in a shaker incubator. In some embodiments, shaking ca be conducted at about 10-300 rpm for up to about 24 hours. In some embodiments, shaking can be conducted for about 20, 40, 60, 120, 240, 260, 5, 6, 7, 8, 9, 10, 11, 12, 13, 14, 15, 16, 17, 18, 19, 20, 21, 22, 23 or 24 hours.

During washing/heating 110, the bone marrow derived cells can be lysed. In some embodiments, the bone marrow derived cells can be lysed using a lysing solution containing water, salt, or an acid. In some embodiments, the lysing solution is just water. In some embodiments, the washing solution and the lysing solution can be the same solution. The acid can be acetic acid, formic acid, trichloroacetic acid, hydrofluoric acid, hydrocyanic acid, hydrogen sulfide, or hydrochloric acid. In some embodiments, the lysis solution contains about 0.001M to about 1M acetic acid. In some embodiments the lysing solution that contains the bone marrow and/or marrow-rich bone is mixed with pre-heated water. In some embodiments, the bone marrow or marrow-rich bone is lysed for about 60 minutes. In other embodiments, the bone marrow or marrow-rich bone is incubated in the lysing solution with shaking. In other embodiments, the lysing conditions can include, but are not limited to, ultrasonic techniques, thermolysis (e.g. freeze/thaw cycling), microfluidic techniques, osmotic shock, electric shock, homogenization, French press, impingement, excessive shear (e.g. aggressive pipetting through a small aperture, centrifuging at excessive revolutions per minute resulting in high gravity forces), pressure, vacuum forces, milling or bead beating techniques that physically collide or grind cells to mechanically break cell membranes, pH shock, exposure to detergents, enzymes, viruses, solvents, surfactants, hemolysins, or combinations thereof.

After washing/lysing 110, the lysate can be optionally fractionated via centrifugation 130 to separate out particles present in the lysate based on their size or density. Such centrifugation techniques that can be employed include, but are not limited to, differential centrifugation, rate-zonal centrifugation, and isopycnic centrifugation. In embodiments where centrifugation is used to separate particles in the lysate based on density, a suitable density gradient medium can be used. Suitable density gradient mediums include, but are not limited to, sucrose, glycerol, sorbitol, Ficoll® medium, polysucrose, dextrans, CsCl, $Cs_2SO_4$, KBr, Diatrizoate, Nycodenz® medium, Histodenz™ medium, iodixanol, Histopaque® mediums, ACCUSPIN® medium, and Percoll® medium. One of ordinary skill in the art will appreciate that the type of medium used is dependent on the type of particle(s) that is desired to be separated out. One or more rounds of centrifugation can be applied to the lysate to further separate out different particles in the lysate. In some embodiments, the desired fraction contains a bioactive factor, such as, but not limited to, a cytokine or osteoinductive protein. In some embodiments, the lysate is centrifuge at about 100 to about 20000 rpm for about 1 to about 600 minutes. In some embodiments, the lysate is centrifuged at about 4000×g for about 10 minutes at about 4° C.

After the optional fractionation 130, the desired fraction can be removed from the centrifuged lysate. In some embodiments, the desired fraction contains one or more bioactive factor, such as, but not limited to, a cytokine or osteoinductive protein. The bioactive factor containing fraction can then be dehydrated 140 using a suitable technique.

Suitable dehydrating techniques include, but are not limited to, evaporation, vacuum drying, lyophilization, freeze drying, sublimation, and precipitation. After dehydration, the soluble protein composition can contain an acid, such as glutamic acid, that can be reconstituted along with the proteins and other bioactive factors that can be present in the soluble protein composition.

Figure 2:
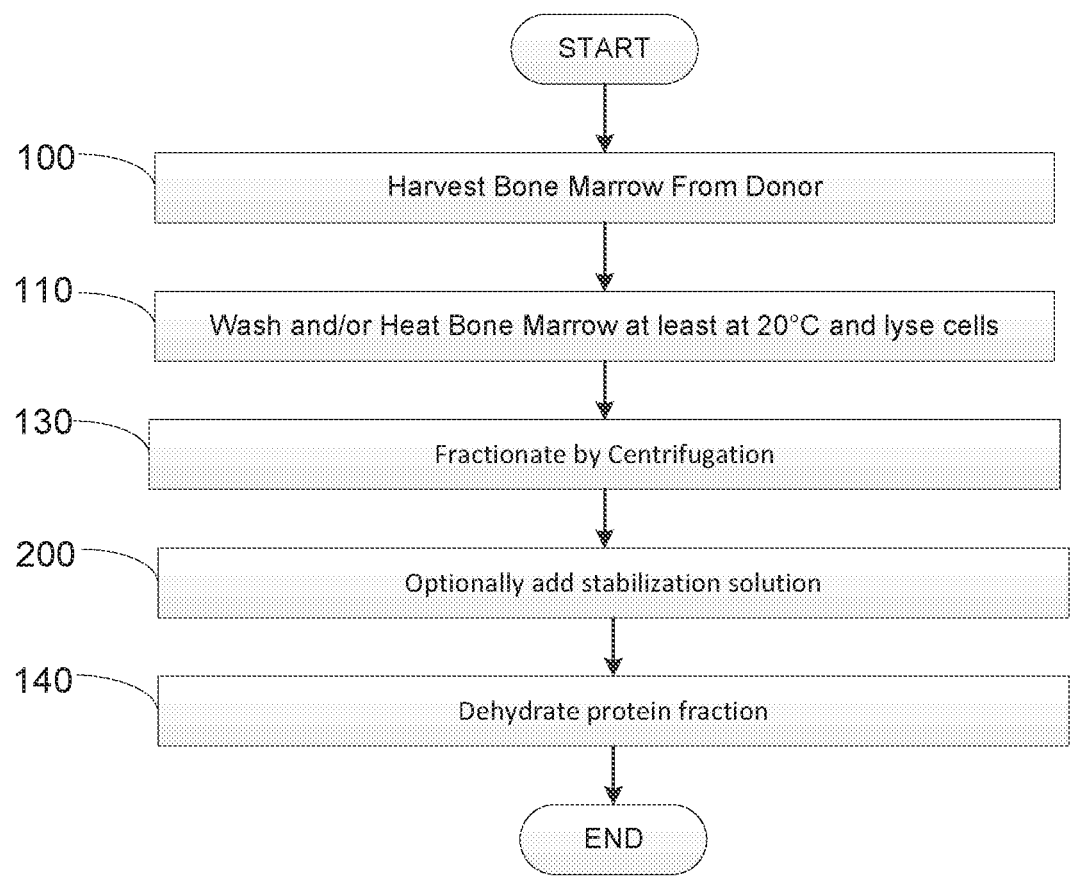
FIG. 2 is a flow diagram showing another embodiment of a method to produce soluble bone marrow derived proteins.

With the general process described, attention is directed to FIGS. 2-10, which demonstrate various embodiments of the general method of producing a soluble bone marrow derived soluble protein composition. Discussion begins with FIG. 2, which demonstrates embodiments of a method of generating a soluble bone marrow derived protein composition. As in FIG. 1, bone marrow can be harvested 100 and washed/heated and bone marrow derived cells can be lysed 110. The desired components (e.g. bioactive factors) of the resulting lysate can be optionally separated from the undesirable components using by fractionating using a suitable centrifugation technique 130. Once the desired fraction containing the proteins and/or bioactive factors of interest is obtained, the desired fraction can be dehydrated 140 using a suitable dehydration technique. As shown in FIG. 2, an optional suitable stabilization solution can be added 200 prior to dehydration 140. Suitable stabilization solutions can aid in maintaining protein integrity and activity. In some embodiments, the stabilizer can include sucrose, trehalose, glycine, L-glutamic acid, sodium chloride, polysorbate-80 and combinations thereof. The stabilization solution can contain preservatives, antibiotics, antivirals, antifungals, pH stabilizers, osmostablizers, anti-inflammants, anti-neoplastics, chemotherapeutics, immunomodulators, chemoattractants, growth factors, anticoagulants, or combinations thereof. In some embodiments, the stabilization solution per cc of final product can be about 1 mg Sucrose, 5 mg Glycine, 3.7 mg l-Glutamic Acid, 0.02 mg NaCl and 0.02 mg Polysorbate-80.

Figure 3:
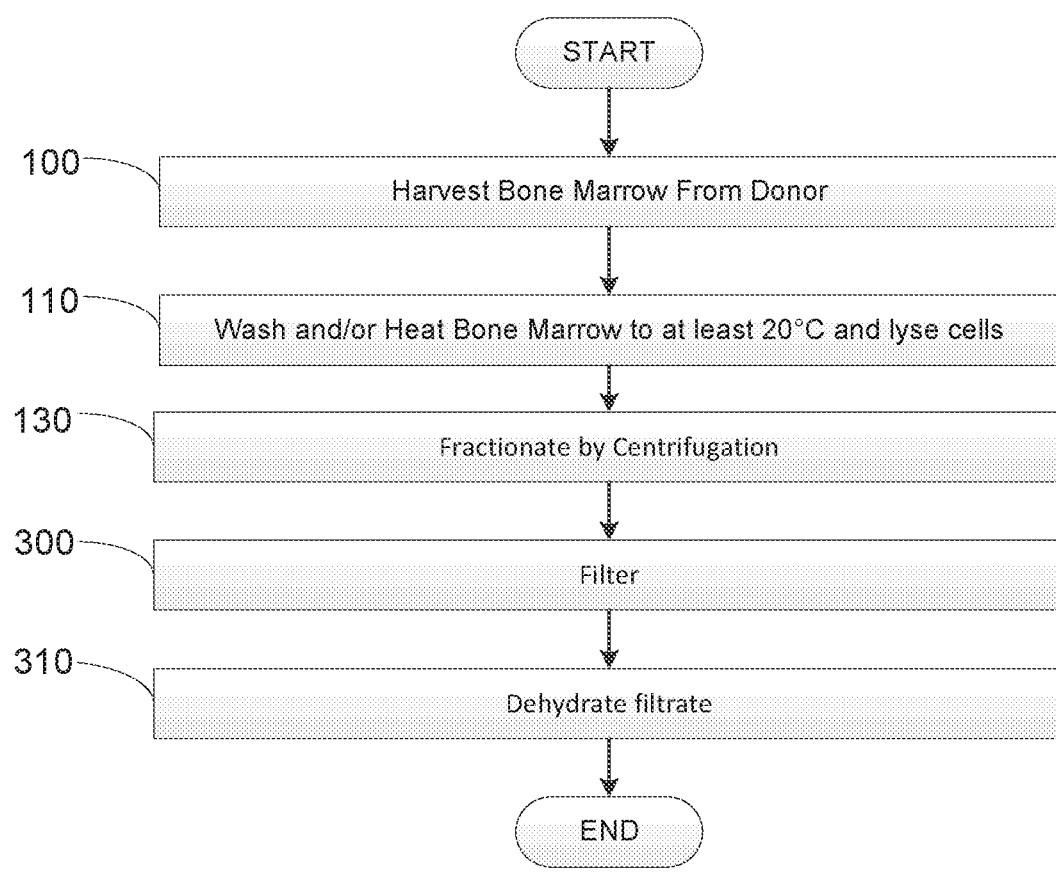
FIG. 3 is a flow diagram showing another embodiment of a method to produce soluble bone marrow derived proteins.

Discussion continues with FIG. 3, which shows another embodiment of a method of producing a soluble bone marrow derived soluble protein composition. As in FIG. 1, bone marrow can be harvested 100 and washed/heated and lysed 110. The desired components (e.g. bioactive factors) of the resulting lysate can be optionally separated from the undesirable components using by fractionating using a suitable centrifugation technique 130. As shown in FIG. 3, after fractionation by centrifugation 130 the fraction containing the desired components can be further filtered using a suitable filtration technique to remove additional undesired components that can remain in the fraction. Suitable filtration techniques can include, but are not limited to, size exclusion techniques and/or affinity purification techniques, immunoseparation techniques, and charged based separation techniques. In some embodiments, additional undesired components can include, but are not limited to, nucleic acids such as DNA and RNA, and other compounds such as hemoglobin, globin proteins, cell fragments, cell membrane molecules and other molecules that can stimulate an immune response in a subject. In some embodiments, the filter can be low protein binding. In some embodiments, the filter can be high DNA binding.

In some embodiments, the filter can preferentially bind one growth factor over another growth factor (such as, but not limited to, BMP-2, BMP-7, VEGF, aFGF, bFGF, IGF, HGF, or combinations thereof). Suitable materials for some filters used in the filtration step 300, include, but are not limited to, Teflon® membranes, nylon membranes, PVDF (polyvinylidene) membranes, polypropylene, cellulose acetate, PES (polyethersulfone), regenerated cellulose, glass fiber, and PTFE (polytetrafluorethylene. In some embodiments, the filter can have a size cutoff of about 0.1 to about 3.0 µM. In some embodiments multiple filters can be used, such as in a serial filtration system. In such a system, multiple types of filters can be used. The system can include at least two filters that differ in material and size cut offs. In some embodiments, polypropylene filters (e.g. size cut offs of 30 µm and 10 µm can be used), a glass fiber filter with a size cutoff of about 2.7 µm can be used, and/or a series of cellulose acetate filters (8 µm, 5 µm, 3 µm, 1.2 µm, 0.8 µm, 0.45 µm and final one of 0.2 µm) can be used to filter. The filters can be configured as syringe filters, disc filters, vacuum filter systems, bottle top vacuum filters, tube top vacuum filters, or centrifuge tube filters.

Figure 4:
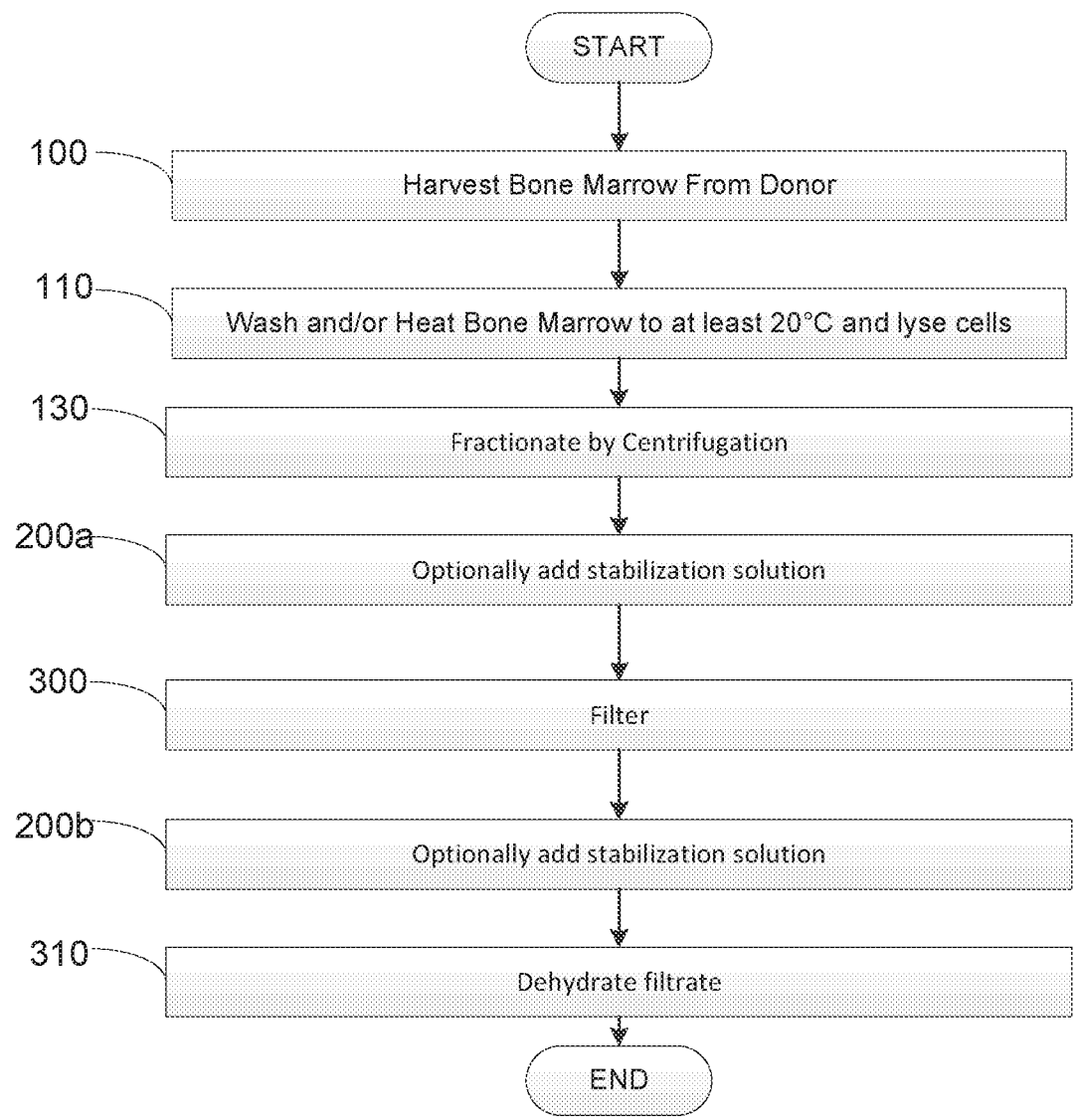
FIG. 4 is a flow diagram showing another embodiment of a method to produce soluble bone marrow derived proteins.

The filtrate obtained after filtering 300 can contain the desired soluble bone marrow derived proteins. The filtrate can also contain acid that can be used during the lysing step 110. The filtrate can be dehydrated 310 using any suitable dehydration techniques. Suitable dehydration techniques are described with respect to dehydrating the protein fraction 140 in FIG. 1. As shown in FIG. 4, an optional suitable stabilization solution can be added 200 a,b to the product prior to dehydration 310. The stabilization solution can be added after centrifugation 130 and/or after filtration 300. Suitable stabilization solutions are described elsewhere herein with respect to FIG. 2.

While the bone marrow can be heated 110 to facilitate better penetration of lysing solution or viscosity reduction and/or removal of the undesired adipocytes that can be present in bone marrow tissue, in some instances it can be desirable to further filter the harvested bone marrow prior to or during lysing of the bone marrow desired cells.

Figure 5:
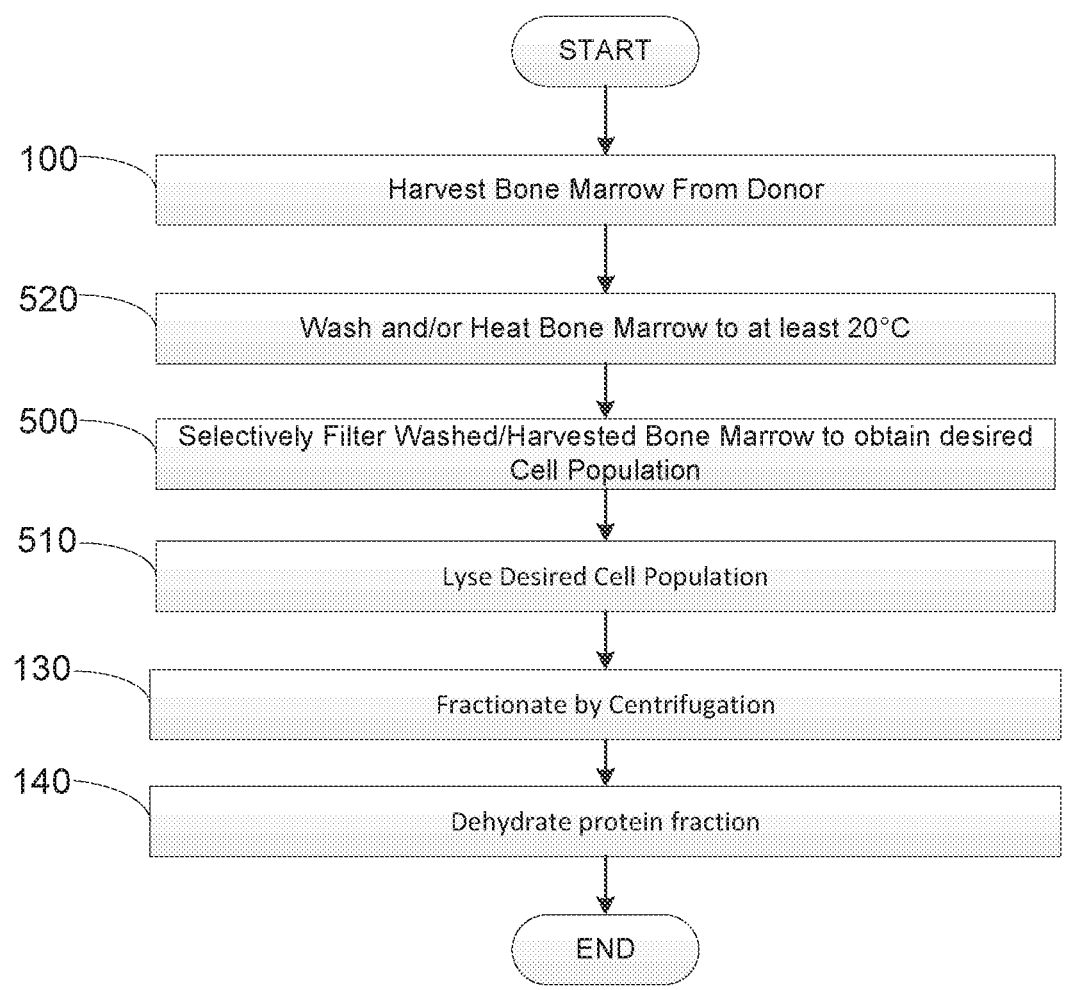
FIG. 5 is a flow diagram showing another embodiment of a method to produce soluble bone marrow derived proteins.

As shown in FIG. 5, bone marrow can be harvested 100 from a donor as previously described in reference to FIG. 1. The harvested bone marrow can then be washed/heated 520 as previously described with respect to FIG. 1. In some embodiments, the bone marrow cells are not all lysed during the washing step. The non-lysed cells can be further separated to obtain a desired cell population. The washed/heated bone marrow can then be selectively filtered to obtain a desired cell population 500. Selective filtering can be completed by any suitable filtering techniques including, but not limited to, size exclusion separation techniques, affinity separation techniques, immunoseparation techniques, charge separation techniques, and chromatography techniques. For example, selective filtering can be achieved using osmotic lysis, cytolysis, centrifugation, size exclusion chromatography, ion exchange chromatography, expanded bed absorption chromatography, affinity chromatography (including but not limited to supercritical fluid chromatography), displacement chromatography, gas chromatography, liquid chromatography, column chromatography, planar chromatography (including, but not limited to paper chromatography, thin-layer chromatography), reverse-phase chromatography, simulated moving-bed chromatography, pyrolysis gas chromatography, fast protein liquid chromatography, high performance liquid chromatography, ultra-high performance liquid chromatography, countercurrent chromatography, chiral chromatography and solid phase extraction. In some embodiments, where bmMSC are desired, osmotic lysis can be used to select for bmMSC as they are resistant to cytolysis and osmotic lysis.

In some embodiments, the bone harvested bone marrow can be selectively filtered to obtain a desired cell population, such as bone marrow MSCs, prior to washing and lysing the bone marrow cells. In these embodiments, the washing and lysing can be performed under heating and can be as described as set forth in FIG. 1, step 110.

After selective filtering of the bone marrow derived cells 500 the remaining desired cell population is lysed 510. Suitable lysing techniques are described with respect to FIG. 1. After lysing, the desired cell population can be fractionated 130 by centrifugation as previously described with respect to FIG. 1. Finally the obtained desired fraction containing the desired bone-marrow derived proteins and/or other bioactive factors can be dehydrated as previously described with respect to FIG. 1.

Figure 6:
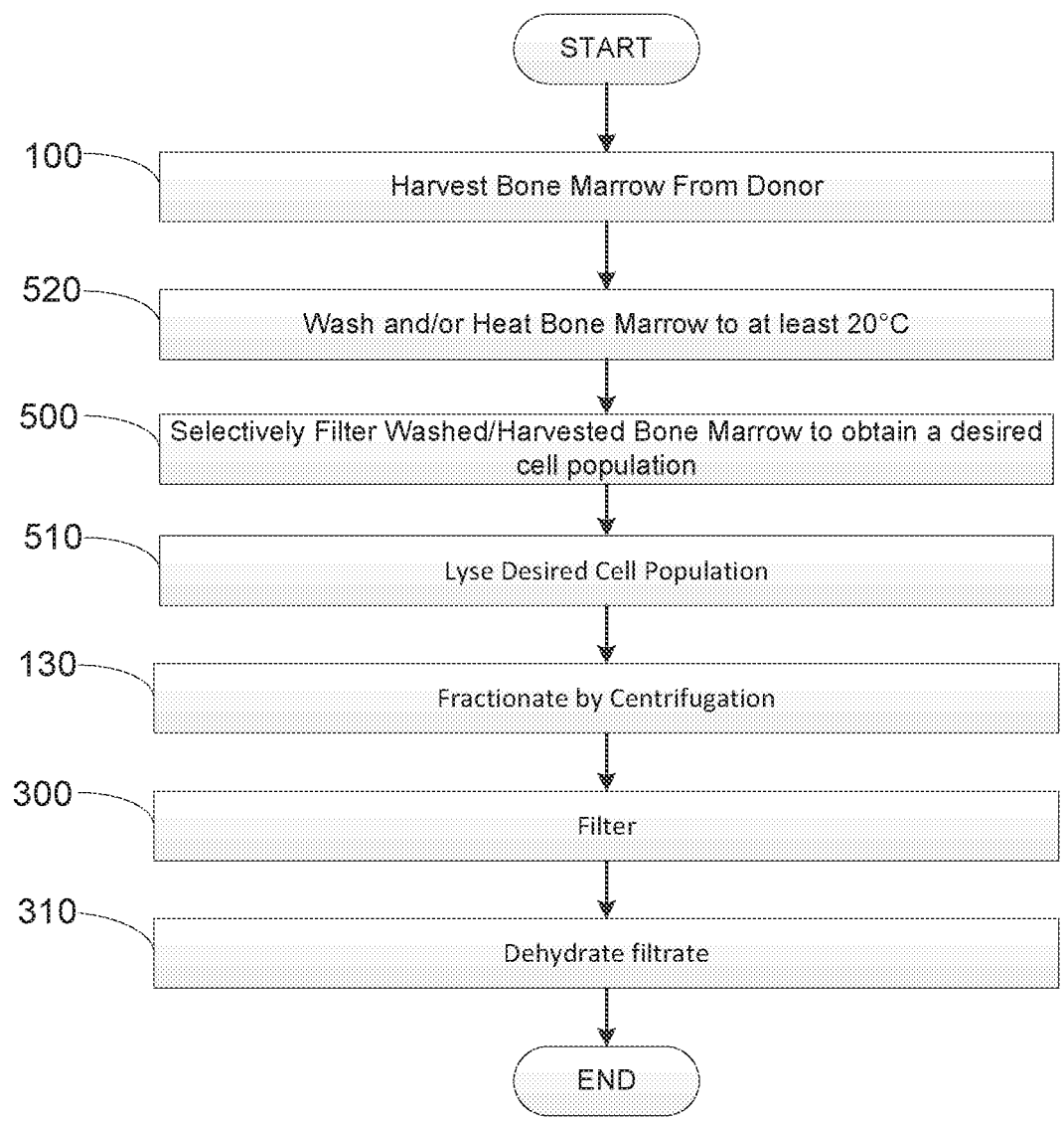
FIG. 6 is a flow diagram showing another embodiment of a method to produce soluble bone marrow derived proteins.
Figure 7:
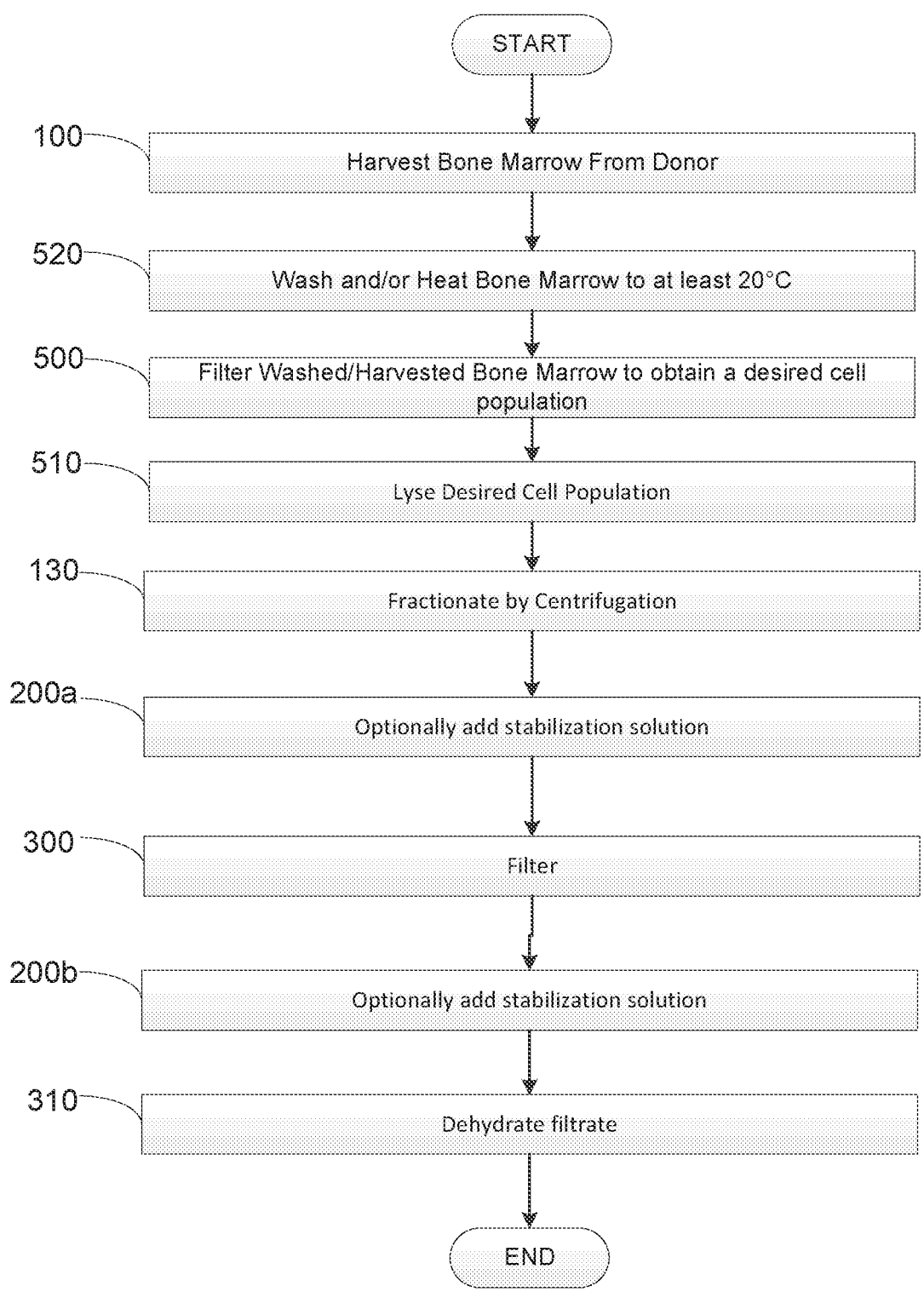
FIG. 7 is a flow diagram showing another embodiment of a method to produce soluble bone marrow derived proteins.

As shown in FIG. 6, the method where the harvested bone marrow can be selectively filtered 500 prior during or prior to lysing (FIG. 5) can optionally include the step of filtering 300 the obtained fraction after centrifugation 130. Filtering 300 can be performed as previously described with respect to FIG. 3. After filtering 300, the desired filtrate can be dehydrated 310 as previously described. As shown in FIG. 7, the methods (FIG. 5 and FIG. 6) where the harvested bone marrow can be selectively filtered 500 prior to or during lysing can also include the optional step of adding a stabilization solution 200 a,b after centrifugation 130 and/or filtration 300.

Figure 8:
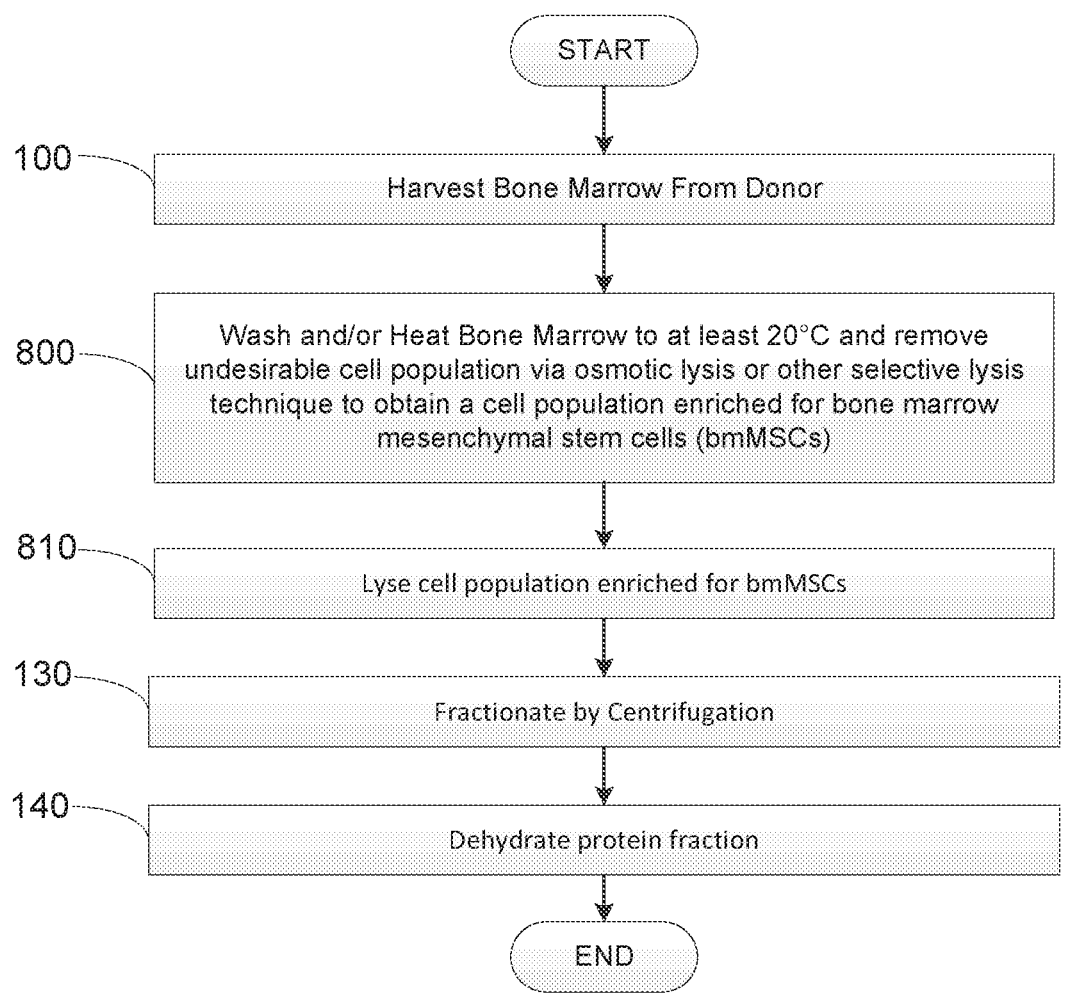
FIG. 8 is a flow diagram showing another embodiment of a method to produce soluble bone marrow derived proteins.

In some embodiments, it can be desirable to obtain proteins or bioactive factors specifically from bmMSCs. As shown in FIG. 8, bone marrow can be harvested from a donor 100 as previously described in reference to FIG. 1. The harvested bone marrow can be washed and heated 110 as previously described in reference to FIG. 1. After washing/heating the harvested bone marrow 110, bmMSC can be separated from the undesirable cell population 800 using osmotic lysis, cytolysis, or other suitable selective lysing technique to produce a population of cells that is completely bmMSCs or enriched for bmMSCs. Suitable selective lysing techniques are described elsewhere herein, for example, in reference to FIG. 5. As previously described, bmMSCs are resistant to osmotic lysis and cytolysis. As such after such treatments, most of the bmMSCs will remain while the other cells will be lysed.

Figure 9:
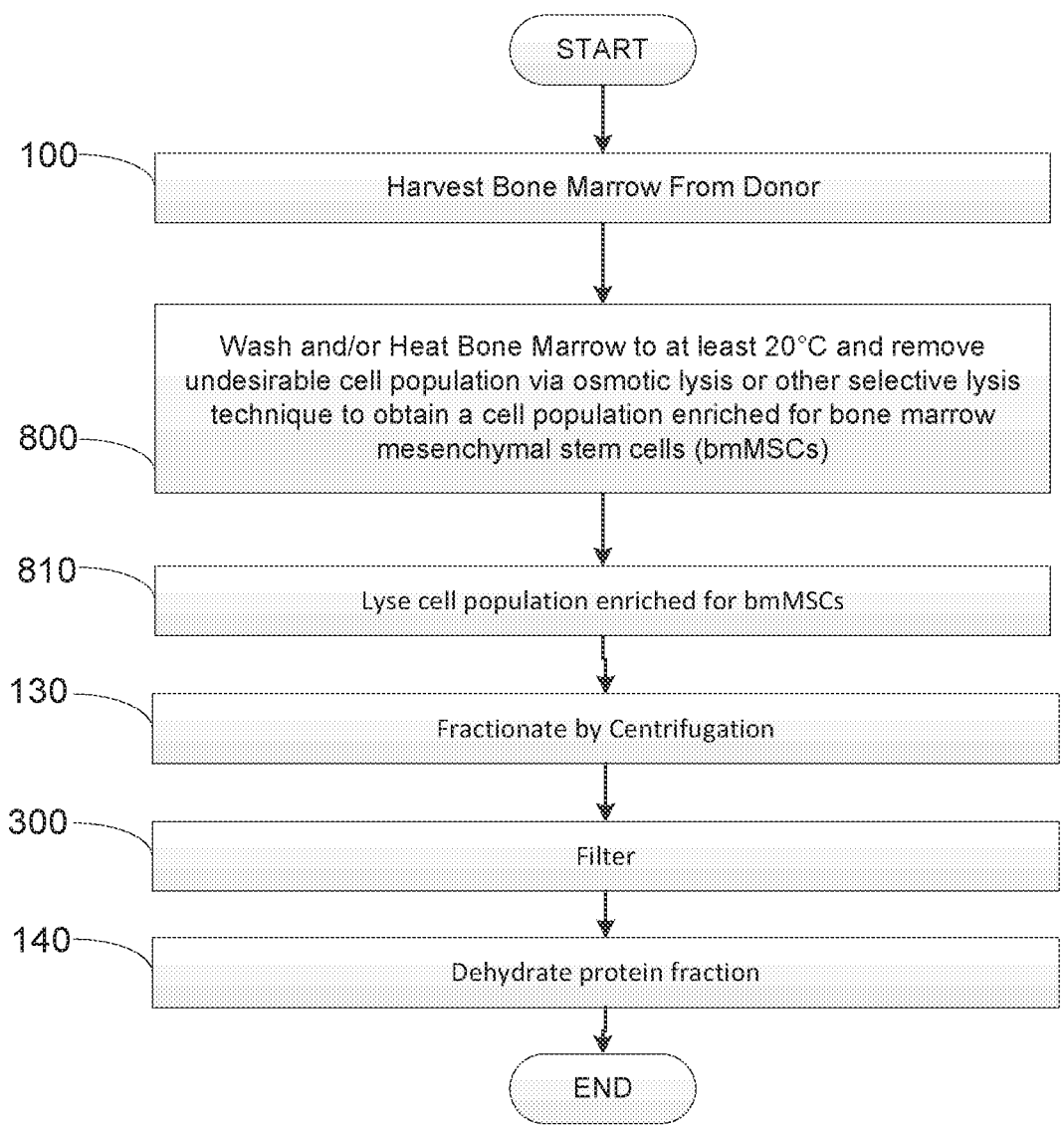
FIG. 9 is a flow diagram showing another embodiment of a method to produce soluble bone marrow derived proteins.
Figure 10:
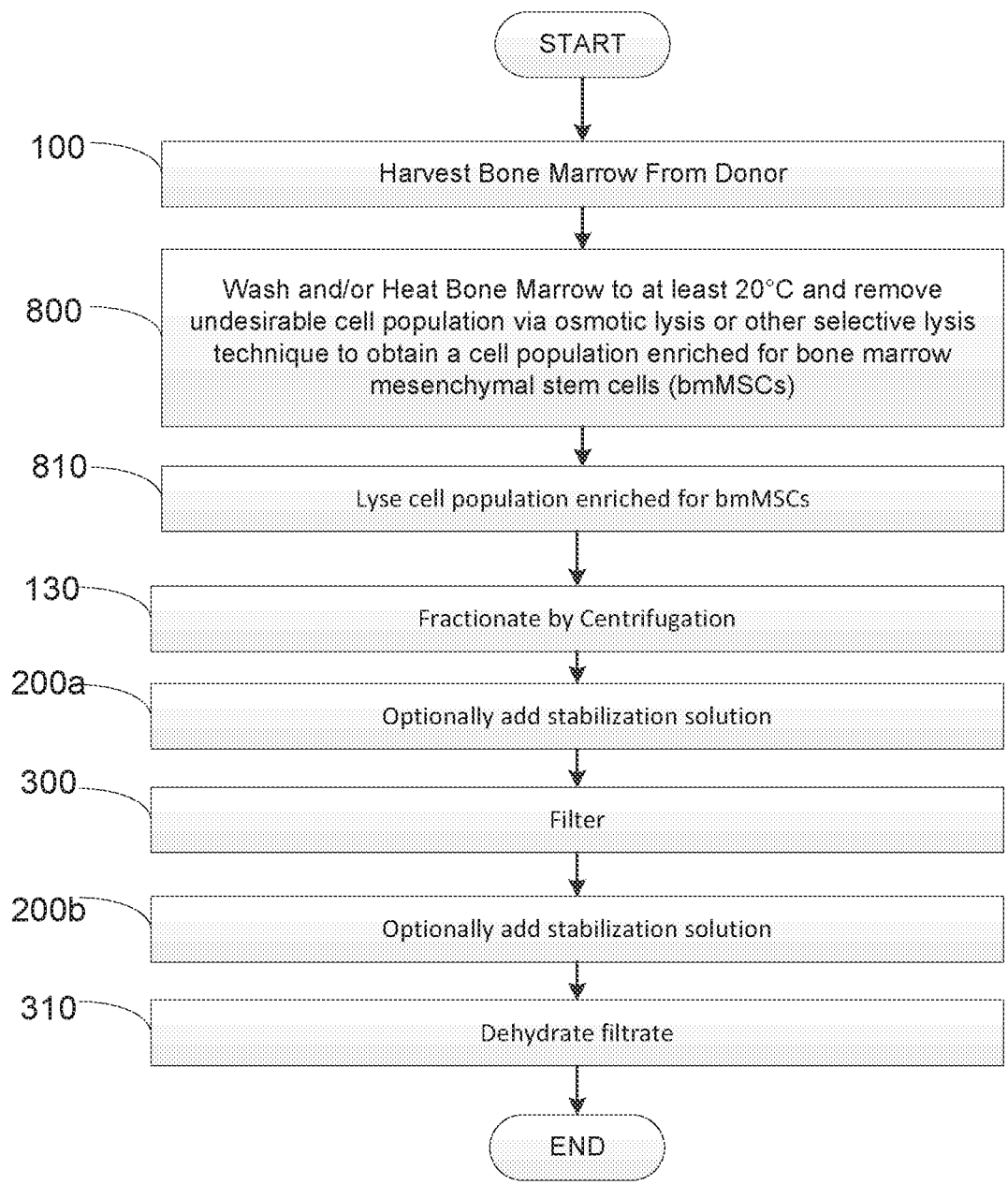
FIG. 10 is a flow diagram showing another embodiment of a method to produce soluble bone marrow derived proteins.

The bmMSCs or the cell population enriched for bmMSCs can be lysed 810 to obtain bmMSC or primarily bmMSC derived proteins and/or other bioactive factors. As previously described, the lysate can be optionally fractionated by centrifugation 130 and the desired proteins and/or bioactive factor containing fraction can be dehydrated 140 as previously described. As shown in FIGS. 9 and 10, the method can include the optional steps of filtering 300 after centrifugation 130 and/or adding a stabilizer 200 a,b after the step of centrifuging 130 and/or filtering 300.

It will be appreciated that other steps can be included in any of the methods described herein. In some embodiments, the method can include a pH altering step where an acid or a base or an acidic or basic solution can be added to product of any step in any method to result in a product that is acidic (pH less than 7), basic (pH greater than 7), or neutral (pH of 7). In some embodiments, after lysing, the lysate or product from any other subsequent step can be made more acidic, neutral, or basic as desired. In embodiments, the dehydrated product containing the soluble bone marrow derived proteins and/or bioactive factor(s) contains an acid that was introduced in the lysing step (e.g. 110, 510, or 810). In other embodiments, the stabilization solution can contain an acid or base that can result in an acidic, basic, or neutral solution.

In some embodiments, the method can include a concentration step, where the product of any step in any embodiment of the method can be concentrated by a suitable technique. Suitable concentration techniques include but are not limited to, dehydration techniques (described elsewhere herein) and centrifugation based techniques. Other concentration techniques will be appreciated by those of skill in the art.

Methods of Making Scaffolds Containing a Soluble Bone Marrow Protein Composition Methods of making the scaffold material, including VITOSS® material or CORTOSS® material, are described in U.S. Pat. Nos. 5,681,872; 5,914,356; 5,939,039; 6,325,987; 6,383,519; 6,521,246; 6,736,799; 6,800,245; 6,969,501; 6,991,803; 7,052,517; 7,189,263; 7,534,451; 8,303,967; 8,460,686; 8,647,614, which are incorporated by reference herein as if expressed in their entirety. Methods of making the dehydrated soluble bone marrow protein compositions are described herein. Methods and techniques of making or obtaining other suitable scaffold materials will be appreciated by those having ordinary skill in the art. In some embodiments, the scaffold material can be introduced during the production of making a soluble bone marrow composition where the scaffold material is mixed in at a step, such as the initial washing and/or lysing step with the initial starting bone marrow material.

Methods of Using the Soluble Bone Marrow Protein Compositions

The soluble bone marrow protein compositions (dehydrated or otherwise formulated as described herein) can contain an acid or be at an acidic pH. The soluble bone marrow protein compositions can be implanted into or otherwise administered to a subject in need thereof. In some embodiments, an effective amount of the soluble bone marrow derived protein composition (dehydrated or otherwise formulated) can be implanted or otherwise administered to a subject in need thereof. When implanted or administered, the proteins and/or other bioactive factors and the acid can be diluted and/or reconstituted by the bodily fluids of the subject. When this occurs, an acid microenvironment surrounding the proteins and/or other bioactive factors can be created. The acidic microenvironment surrounding the soluble bone marrow protein composition can facilitate solublization of the bone marrow derived proteins and/or other bioactive factors in the composition and can also facilitate the binding of the bone marrow proteins and/or other bioactive factors a scaffold (natural or synthetic), bone, cartilage, or other tissue of the subject at the site where the soluble bone marrow protein composition is deposited within the subject.

The soluble bone marrow protein compositions (dehydrated or otherwise formulated as described herein) can be added to a suitable scaffold or device. Suitable scaffolds include, but are not limited to, allogeneic, autologous, syngeneic, or xenogeneic complete extracellular matrix, decellularized extracellular matrix, or extracellular matrix components, hydrogels, synthetic or natural polymer solids and semi-solids, carbohydrates, self-assembling peptides, carbon nanotubes, collagen, calcium salts, chitosan, alginate, hyaluronic acid, bone powder, cartilage powder, proteins, sugars, plastics, metals, or combinations thereof. In some embodiments, the scaffold can be biocompatible. In other embodiments, the scaffold can be allogeneic, xenogenic, or autologous bone or demineralized bone. The scaffold can be flowable or non-flowable.

Figure 11:
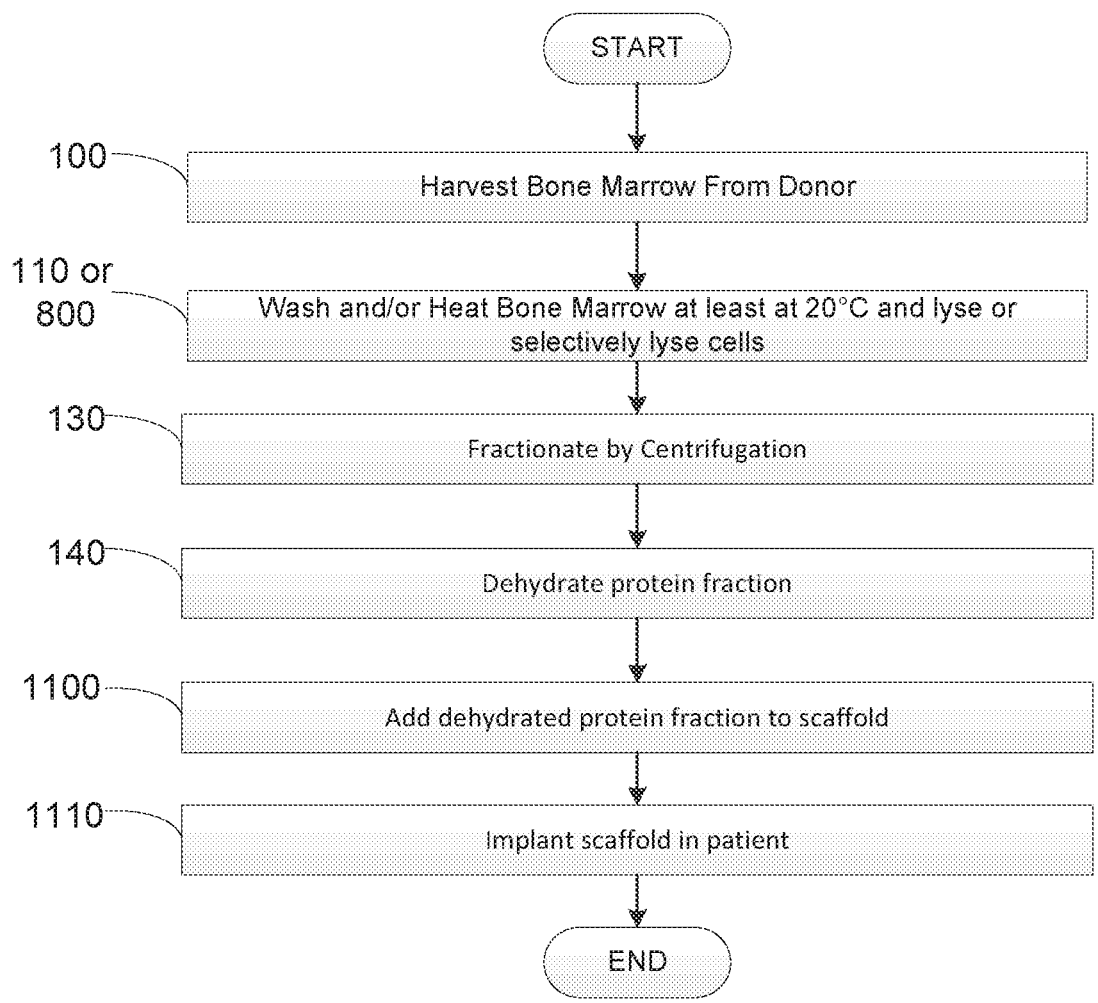
FIG. 11 is a flow diagram showing another embodiment of a method to produce soluble bone marrow derived proteins.

As shown in FIG. 11, the soluble bone marrow protein composition can be applied to a scaffold (implant) 1100, which is already present in a subject or can be implanted into a subject in need thereof 1110. When implanted 1110, the proteins in the dehydrated soluble bone marrow derived protein composition can solubilize and/or bind the scaffold when they come in contact a bodily fluid present in the subject. The acid present in the dehydrated soluble bone marrow derived protein composition can create an acidic microenvironment where the scaffold and/or soluble bone marrow protein composition is. The acidic microenvironment can facilitate solubilization of the bone marrow derived proteins and/or binding of the proteins and/or other bioactive factors to the scaffold (synthetic or natural) and/or other bone or tissue of the subject that are at the site of implantation. In some embodiments, the soluble bone marrow protein composition can be added in a dehydrated state to an implant material to encapsulate the proteins such as a putty, gel, or suspension.

In other embodiments, the soluble bone marrow derived protein composition can be applied directly into a scaffold already present in the subject in need thereof. As previously described, the proteins and/or other bioactive factors can be diluted or reconstituted when contacted with a bodily fluid present within the subject. As also described above, the acid that can be present in the bone marrow protein compositions described herein can create an acidic microenvironment that can facilitate solubilization and/or binding of the bone marrow proteins and/or bioactive factors to a scaffold present in the subject.

In some embodiments, the method can include the step of implanting or otherwise administering a soluble bone marrow protein composition or scaffold incorporating a soluble bone marrow protein composition as described herein to a subject in need thereof. In some embodiments, a method of treating a subject in need thereof can include the step of implanting or otherwise administering a soluble bone marrow protein composition or scaffold incorporating a soluble bone marrow protein composition as described herein to the subject in need thereof.

In some embodiments, the subject in need thereof needs a bone graft or bone fusion. In some embodiments, the subject in need thereof has a bone and/or joint fracture or disease. In some embodiments, the subject in need thereof needs a spinal fusion. In some embodiments the compositions described herein can be used in patients with low bone density to prophylactically help reduce, delay, or prevent bone loss or fracture.

Methods of Using the Scaffolds Containing a Soluble Bone Marrow Protein Composition The scaffold containing a soluble bone marrow protein composition as provided herein can be implanted in or otherwise administered to a subject in need thereof. The subject in need thereof can be in need of a bone grafting or bone fusion procedure. As such, in some embodiments a method can include the step of implanting or administering an implant containing the scaffold material described herein (including those scaffolds containing a soluble bone marrow protein composition) to a subject in need thereof. In some embodiments, the subject in need thereof can be in need of a bone graft or a bone fusion. In some embodiments, a method of treating a subject in need thereof can include the step of implanting or administering an implant containing a scaffold (including those scaffolds containing a soluble bone marrow protein composition) described herein to a subject in need thereof. In some embodiments, the subject in need thereof is in need of a bone graft or a bone fusion. In some embodiments, the subject in need thereof has a bone fracture, diseased bone, joint fracture, or diseased joint.

Spinal Fusion and Grafting. Many patients affected by severe back pain due to degeneration of one or more discs are often treated with spinal surgical procedures. It is estimated that each year at least 500,000 spinal fusion procedures are performed in the United States. In cases where the patient has advanced disc degeneration or spinal instability, a fusion procedure can involve a surgical incision in the patient's back or abdomen to access and remove the affected disc material. To provide initial stability and support of the surrounding vertebrae, the resulting defect can be filled with a structural implant made of either titanium, shaped bone derived from a human cadaver, or a synthetic material known as polyetheretherketone ("PEEK"). Adjunctively, these procedures can require the use of bone grafting material to repair defects and facilitate the fusion of two bony elements. A scaffold, such as VITOSS® material, containing the soluble bone marrow protein composition can provide an alternative to patient- or cadaver-derived tissues in spinal fusion and/or grafting procedures. In some embodiments, a method of fusing a portion of the spine, where the method includes the step of implanting or administering an implant containing the scaffold described herein to a subject in need thereof.

Trauma. Physical trauma such as falls and accidents can result in bone fracture or damage. Fractures of broken bones are often realigned with hardware, such as plates, rods and screws. Once the hardware has been used to recreate the skeletal anatomy and to provide the stability of the bony structure, there are often defects or voids in the bone which remain. Those voids may require the use of bone graft material. The goal of bone grafting in trauma applications is to rapidly heal the damaged bone. Approximately 250,000 trauma related bone graft repairs are performed annually on a worldwide basis. The scaffold, such as VITOSS® material, containing the soluble bone marrow protein composition can be used as a bone graft substitute in a variety of trauma applications, including those of the extremities, spine and pelvis.

For patients with poor bone healing, as seen in osteoporotic patients, CORTOSS containing the soluble bone marrow protein composition can be used in a variety of surgical procedures to quickly provide structural stability and reinforcement of the bones after surgery. The surgeon's goal is to repair the patient's bone and enhance the patient's mobility as quickly as possible since prolonged bed rest or inactivity may result in decreased overall health for older or osteoporotic patients. A scaffold, such as CORTOSS® material, containing the soluble bone marrow protein composition can be made as a simple mix-on-demand delivery system that can allow for minimum waste and maximum ease of use and flexibility for the surgeon. The scaffold, such as CORTOSS® material, containing the NR soluble bone marrow protein composition can be configured as an injectable material that is delivered to a subject through a prefilled, unit dose, disposable cartridge.

In some embodiments, a method of fusing a portion of the spine, where the method includes the step of implanting or administering an implant containing a scaffold (including scaffolds containing a soluble bone marrow protein composition) described herein to a subject in need thereof. In some embodiments, a method of bone grafting, where the method includes the step of implanting or administering an implant containing a scaffold (including scaffolds containing a soluble bone marrow protein composition) described herein to a subject in need thereof.

EXAMPLES

Now having described the embodiments of the present disclosure, in general, the following Examples describe some additional embodiments of the present disclosure.

While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 12:
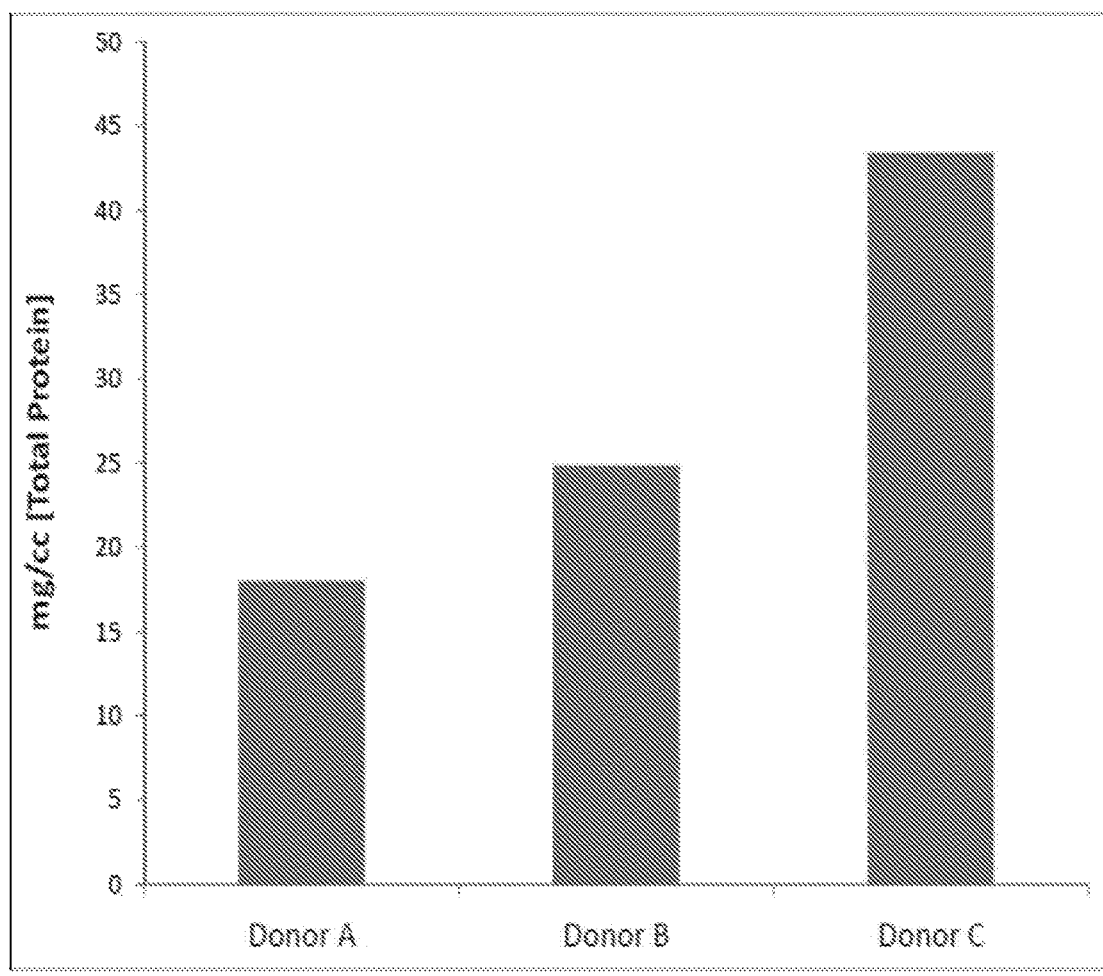
FIG. 12 demonstrates total protein concentration obtained by a method described herein.

FIG. 12 demonstrates total protein concentration obtained by a method described herein. Total protein content was measured using bicinchoninic acid assay (BCA assay). The sample preparation involved reconstituting the dehydrated bone marrow protein composition with either water or saline. FIG. 12 therefore demonstrates the total protein in mg per cc of reconstituted sample soluble bone marrow protein compositions generated from 3 donors (A, B, and C). The testing was conducted according to the manufacturers' instructions (Pierce™ BCA Protein Assay Kit). The total protein concentration is exhibited by a color change of the sample solution from green to purple in proportion to protein concentration, which can then be measured using colorimetric techniques.

Example 2

Figure 13:
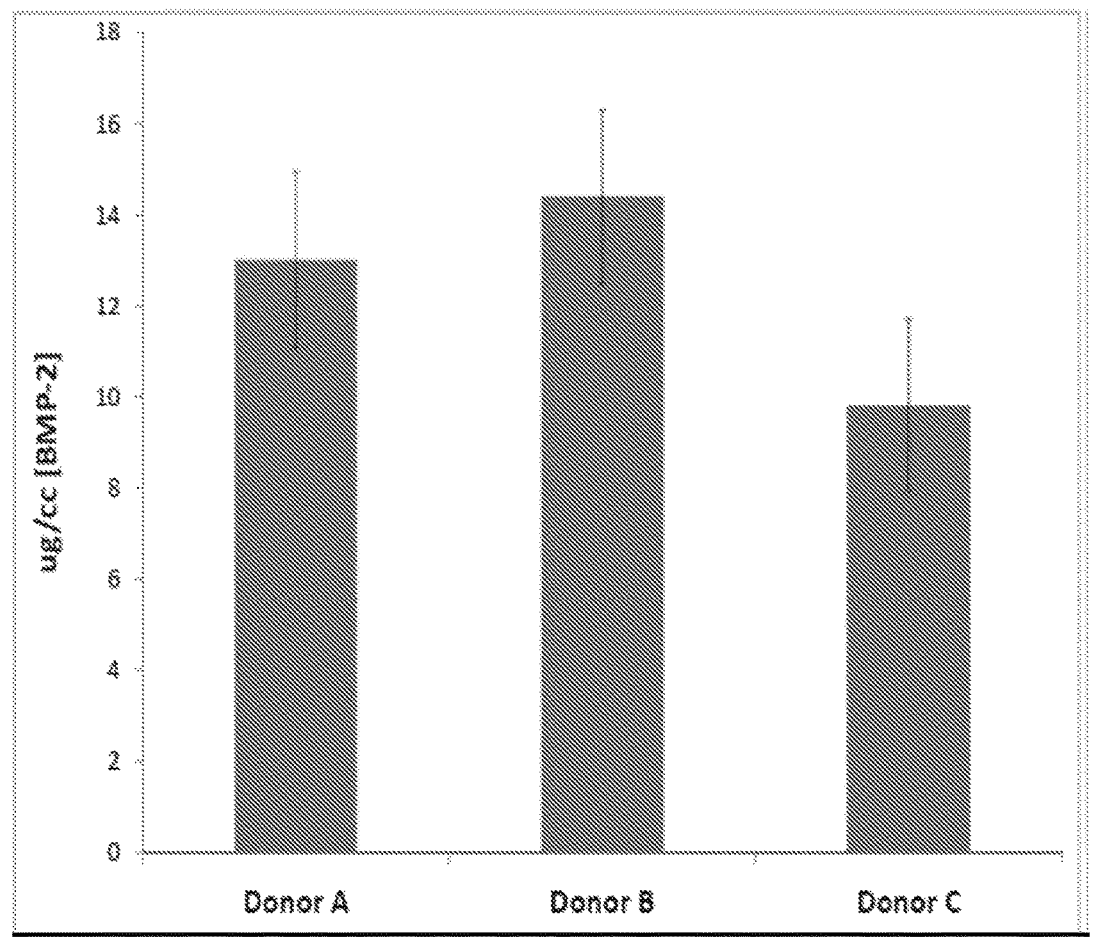
FIG. 13 demonstrates the concentration of BMP-2 protein in a soluble bone marrow compositions described herein derived from various bone marrow donors.

FIG. 13 demonstrates the concentration of BMP-2 protein as measured by an enzyme-linked immunosorbent assay (ELISA) in a soluble bone marrow compositions described herein derived from various bone marrow donors. Here BMP-2 protein was measured in reconstituted or extracted samples from 3 donors (A, B, C) Reconstitution is performed with either water or saline. Extractions are performed in different buffers (Guanidine-HCl or Urea-based buffers) in different concentrations for different incubation times. BMP-2 concentration is expressed as μg BMP-2 per cc of reconstituted or extracted samples.

Example 3

Figure 14:
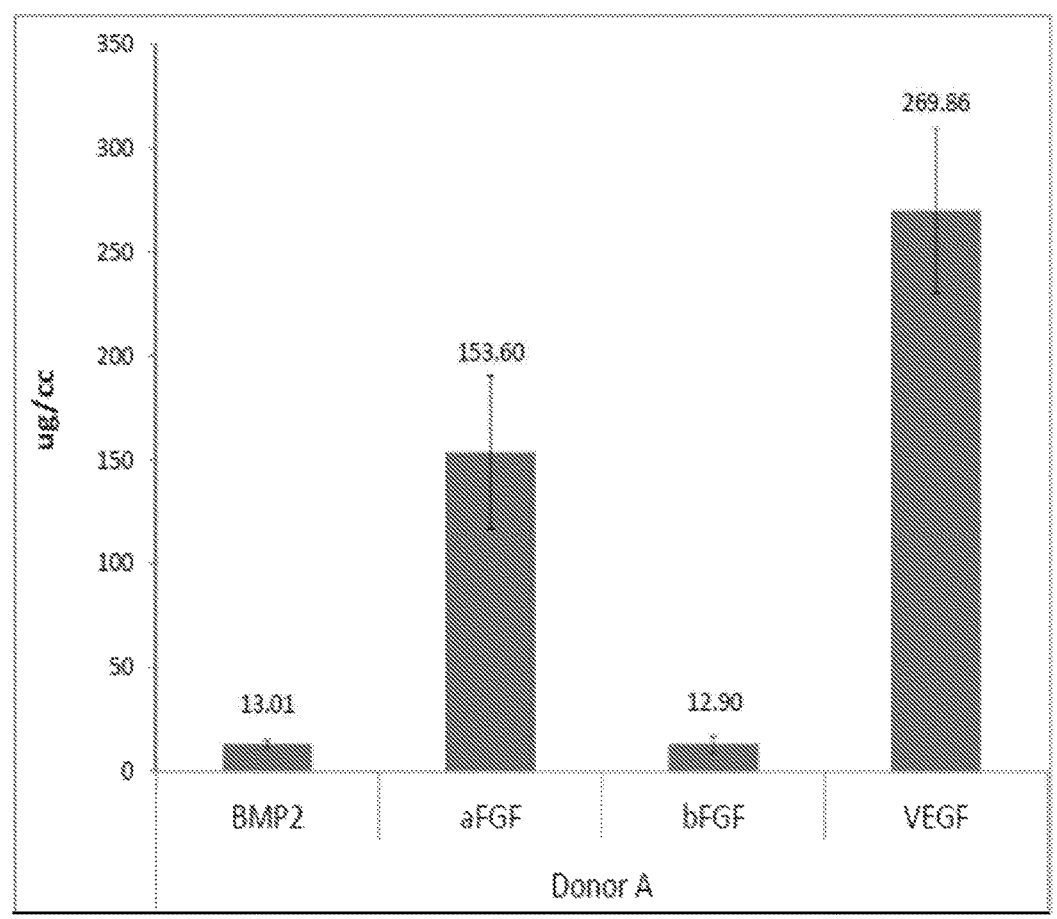
FIG. 14 demonstrates the concentration of various proteins present in a soluble bone marrow composition from various donors.

FIG. 14 demonstrates the concentration of various proteins present in a soluble bone marrow composition from various donors. The growth factors were quantified using ELISA. Test samples were either reconstituted or extracted from various donors (A, B, C). Reconstitution was performed with either water or saline. Extractions are performed in different buffers (Guanidine-HCl or Urea-based buffers) in different concentrations for different incubation times. Bioactive factor concentration is expressed as μg BMP-2 per cc of reconstituted or extracted samples.

Example 4

Figure 15:
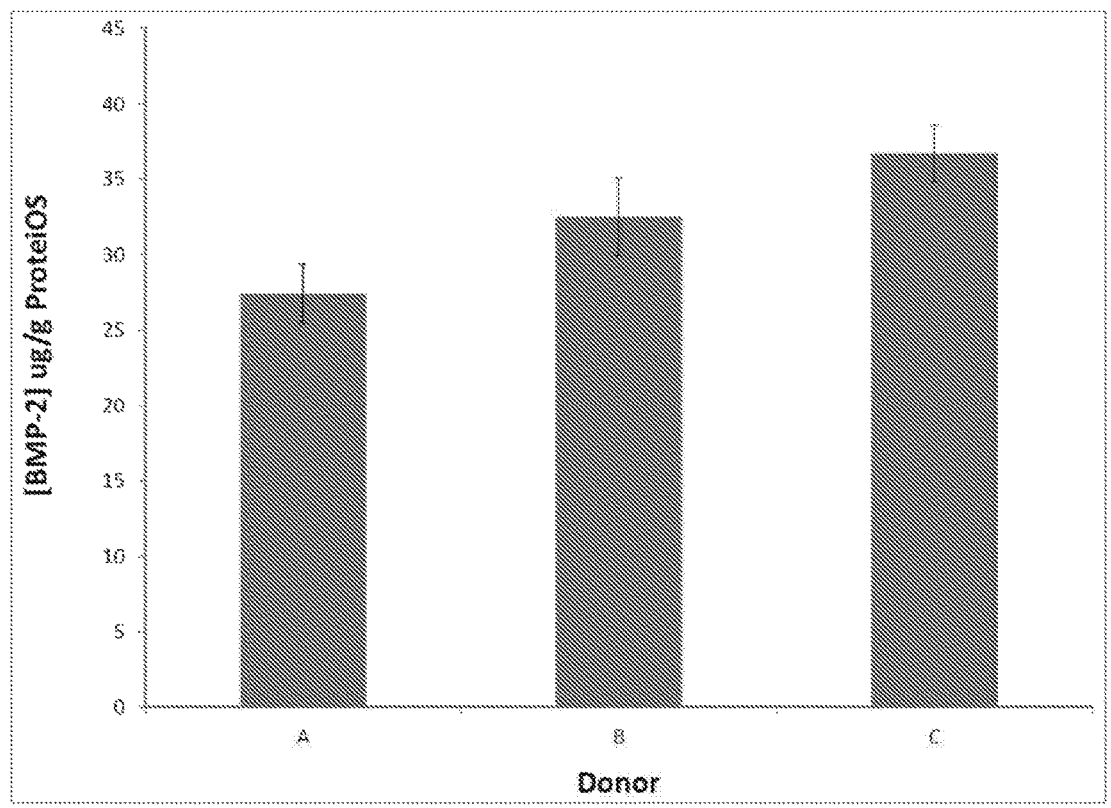
FIG. 15 demonstrates the concentration of BMP-2 ug/g of a soluble bone marrow protein composition (ProteiOS) from various donors.

FIG. 15 demonstrates the concentration of BMP-2 ug/g of a soluble bone marrow protein composition (ProteiOS) from various donors.

Example 5

Figure 16:
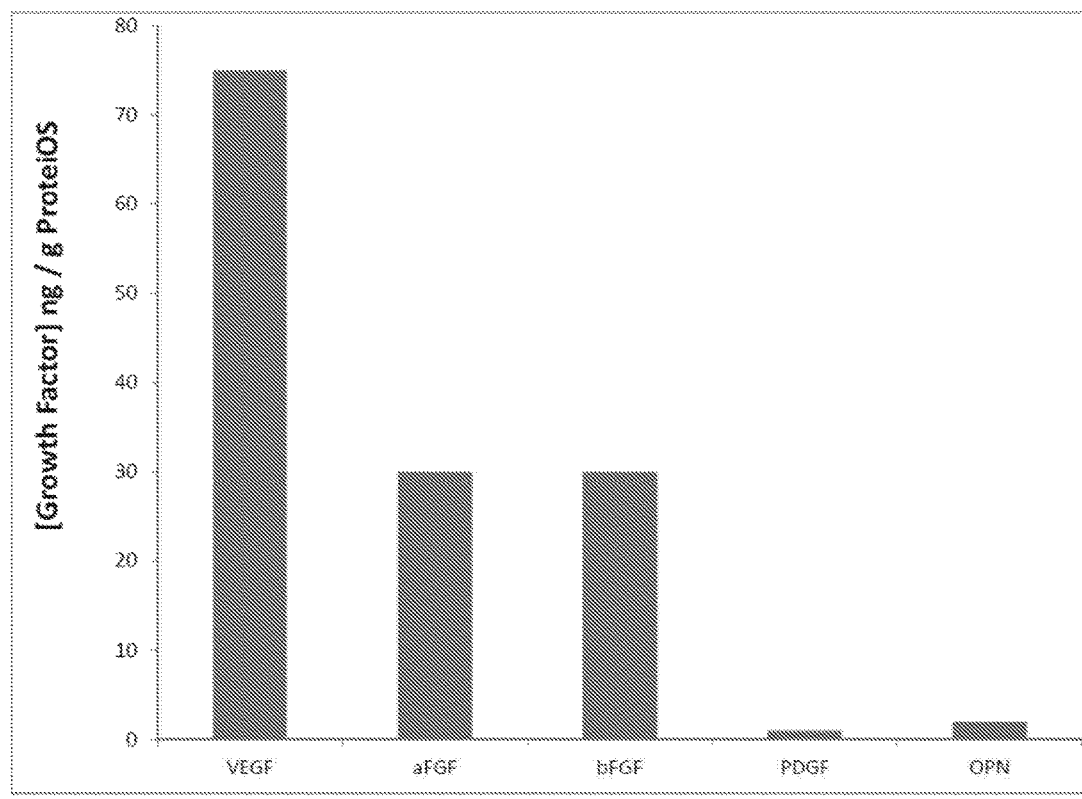
FIG. 16 demonstrates the concentrations of various bioactive factors (ng/g) of a soluble bone marrow protein composition (ProteiOS).

FIG. 16 demonstrates the concentrations of various bioactive factors (ng/g) of a soluble bone marrow protein composition (ProteiOS).

Example 6

Figure 17:
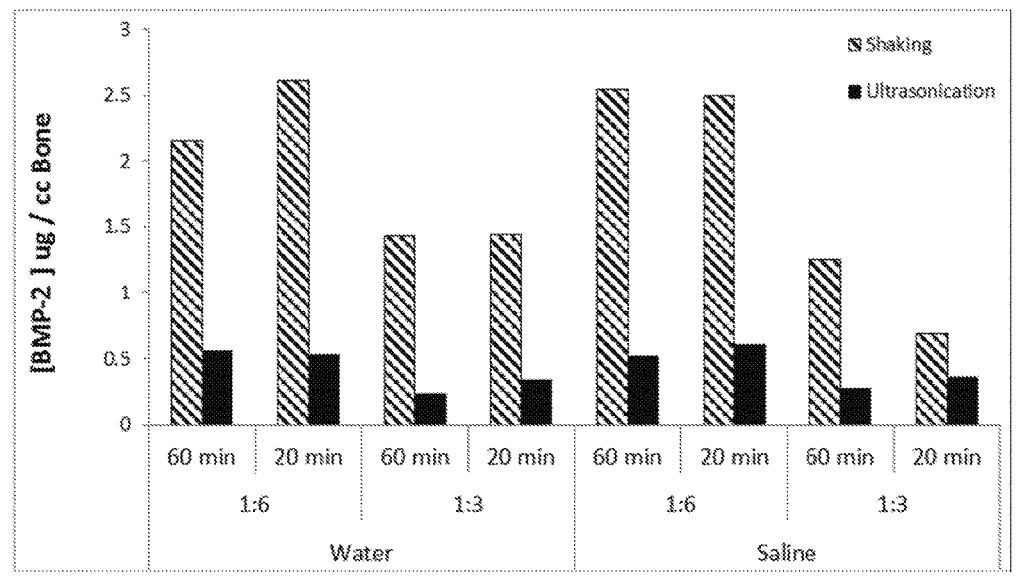
FIG. 17 shows a graph demonstrating BMP-2 content in a soluble bone marrow protein composition per cc of starting bone material obtained under different embodiments of a process to obtain the soluble bone marrow protein composition.

This Example examines the effect of processing time, bioactive factor processing methods (shaking or ultrasonication), processing time (about 20, 40, or 60 minutes) processing solution composition (water or a saline solution), processing temperature (37° C. or 25° C.), and ratio of starting bone material to processing solution (w/v) (1:3 or 1:6) on bioactive factor content in the final soluble bone marrow protein composition. About 3 grams of bone marrow containing material were processed according to the experimental design shown in Table 1. Briefly the starting material was washed in the processing solution at a particular ratio and incubated at a processing temperature and exposed to a processing method for an amount of time. BMP-2 content in the solution obtained was measured using an Enzyme-linked immunosorbent assays (ELISA). The results are demonstrated in FIG. 17.

TABLE 1

| Sample number | Sample ID | Processing Solution | Ratio | Processing Temp | Processing Method | Time |
|---|---|---|---|---|---|---|
| 1 | 6W60S | Water | 1:6 | 37 | Shaking | 60 |
| 2 | 6W40S | | | | | 40 |
| 3 | 6W20S | | | | | 20 |
| 4 | 3W60S | | 1:3 | | | 60 |
| 5 | 3W40S | | | | | 40 |
| 6 | 3W20S | | | | | 20 |
| 7 | 6S60S | Saline | 1:6 | | | 60 |
| 8 | 6S40S | | | | | 40 |
| 9 | 6S20S | | | | | 20 |
| 10 | 3S60S | | 1:3 | | | 60 |
| 11 | 3S40S | | | | | 40 |
| 12 | 3S20S | | | | | 20 |
| 13 | 6W60S25 | Water | 1:6 | 25 | | 60 |
| 14 | 3W60S25 | | 1:3 | | | |
| 15 | 6S60S25 | Saline | 1:6 | | | |
| 16 | 3S60S25 | | 1:3 | | | |
| 17 | 6W60U | Water | 1:6 | 25 | Ultrasonicate | 60 |
| 18 | 6W40U | | | | | 40 |
| 19 | 6W20U | | | | | 20 |
| 20 | 3W60U | | 1:3 | | | 60 |
| 21 | 3W40U | | | | | 40 |
| 22 | 3W20U | | | | | 20 |
| 23 | 6S60U | Saline | 1:6 | | | 60 |
| 24 | 6S40U | | | | | 40 |
| 25 | 6S20U | | | | | 20 |
| 26 | 3S60U | | 1:3 | | | 60 |
| 27 | 3S40U | | | | | 40 |
| 28 | 3S20U | | | | | 20 |

Example 7

In this Example, the effect of adding a rinsing step to the processing step was examined. The initial processing conditions were as follows: the ratio of the bone marrow containing starting material to processing solution was 1:2, the processing solution was water, and the processing conditions were a total of 60 minutes at 37° C. with shaking (See Example 6). Then one or two additional rinse steps were performed. The additional rinse steps can also be thought of as repeating the processing step. The experimental design is set forth in Table 2 and described below.

TABLE 2

| Sample | Starting Material (Marrow-rich Bone) (g) | Starting material:H$_2$O (preheated) | Rinse |
|---|---|---|---|
| A | 10 | 1:2 | Twice for 30 minutes each @ 37° C. |
| B | 10 | 1:2 | Thrice for 20 minutes each @ 37° C. |
| C | 10 | 1:6 | Once for 60 minutes @ 37° C. |

For the processing where one additional rinse (or processing) step was added (for a total of 2 washes or processing steps), the total incubation time was split into two 30 minute incubations, in which one incubation time corresponds to the initial processing step and the second incubation corresponds to the one additional rinse/processing step. For the processing where two additional rinses (or processing) steps were added (for a total of 3 washes or processing steps), the total incubation time was split into three 20 minute incubations, in which one incubation time corresponds to the initial processing step, one incubation time corresponds to the first additional rinse/processing step, and the third incubation time corresponds to the second additional rinse/processing step.

For each additional rinse, the resulting solution was collected from the processing or rinse step that preceded it. Then the same volume of fresh processing solution as the amount of resulting solution collected from the step that preceded it was added to the remaining material. The remaining material was incubated in the fresh processing solution for an additional 30 or 20 minutes (for the one additional or two additional rinses, respectively) at 37° C. with shaking, such that the total incubation time was about 60 minutes. The resulting solution after the final rinse/processing step was collected and maintained in a separate container.

For additional comparison, starting material containing bone marrow was processed using a single processing step using water as the processing solution at a ratio of 1:6. The processing method used was either shaking for 60 minutes at 37° C. or shaking at room temperature (about 25° C.) in deionized water that had been pre-warmed to 37° C.

Figure 18:
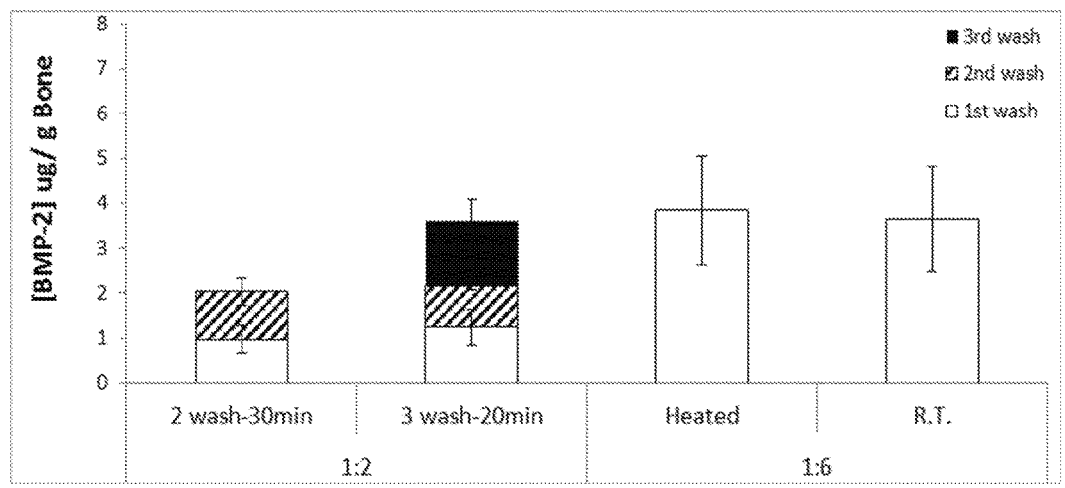
FIG. 18 shows a graph comparing BMP-2 content in a soluble bone marrow protein composition per cc of starting bone material under different processing conditions that include, inter alia, a different number of washing (or rinsing) steps.
Figure 19:
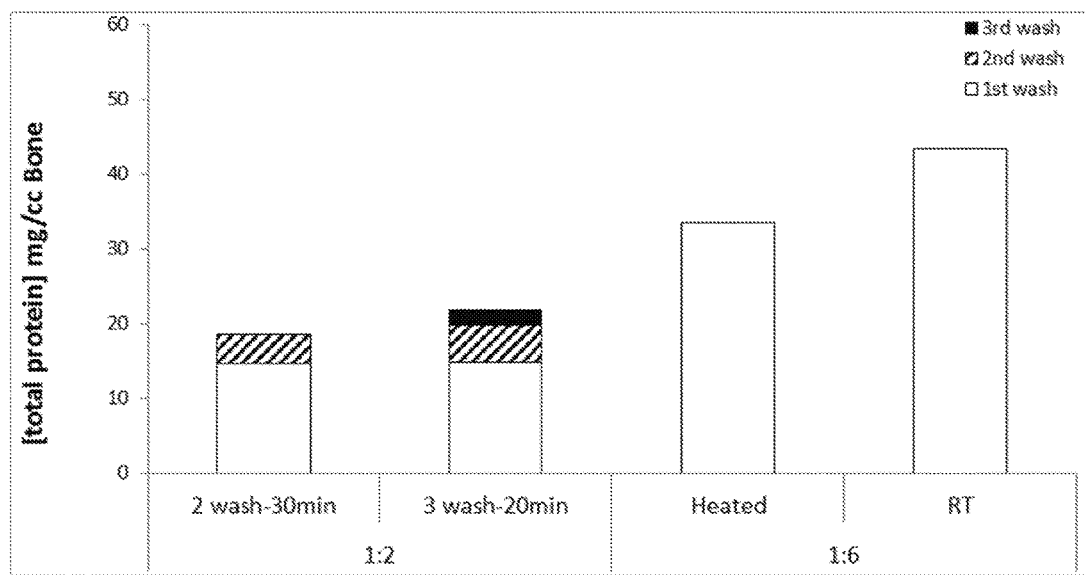
FIG. 19 shows a graph comparing total protein content in a soluble bone marrow protein composition per cc of starting bone material under different processing conditions that include, inter alia, a different number of washing (or rinsing) steps.

The total protein, as measured using a BCA assay, and BMP-2 amount, as measured by ELISA, was measured in each of the collected solutions. The results are demonstrated in FIGS. 18-19.

Example 8

Figure 20:
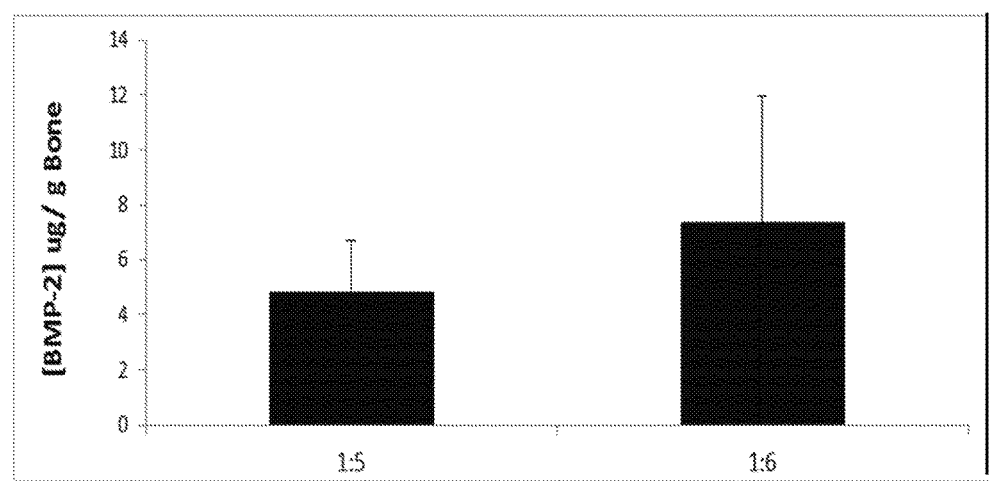
FIG. 20 shows a graph comparing BMP-2 protein content in a soluble bone marrow protein composition processed at different ratios of starting bone material to initial processing solution.
Figure 21:
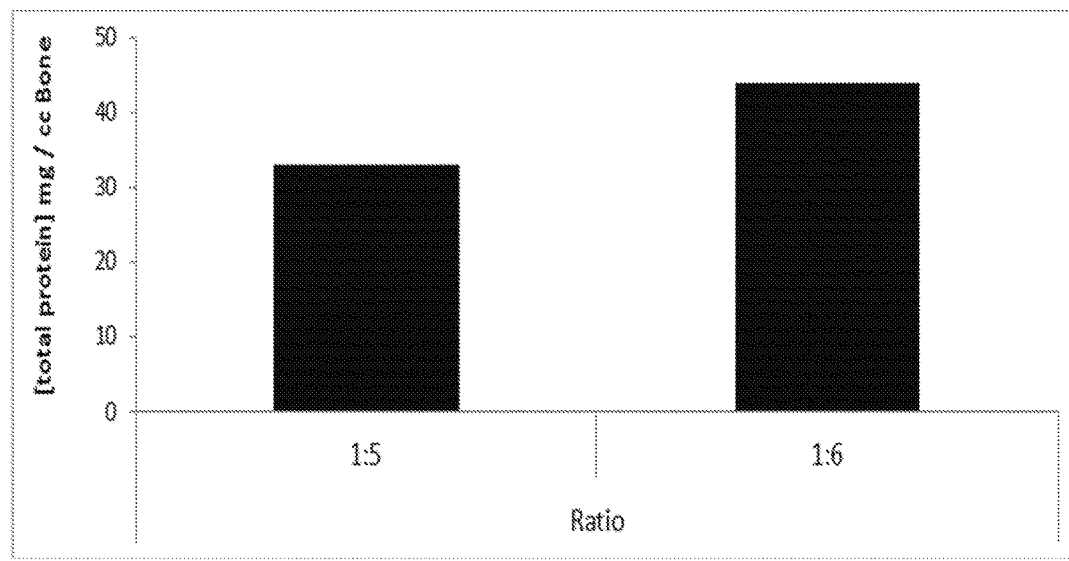
FIG. 21 shows a graph comparing total protein content in a soluble bone marrow protein composition processed at different ratios of starting bone material to initial processing solution.

This Example evaluates the effect the ratio of starting material to processing solution on bioactive factor content in the soluble bone marrow protein composition. The processing of the bone marrow containing starting material was generally as described in Example 7 for the processing method that included one additional rinse/processing step except that the ratio of bone marrow containing starting material to water (w/v) was varied from 1:5 and 1:6, the starting material amount was about 12 g, the processing was conducted at 25° C. using pre-warmed (37° C.) water, and the solutions collected at each step were combined. The study design is presented in Table 3. The total protein, as measured using a BCA assay, and BMP-2 amount, as measured by ELISA, was measured in the final combined collected solution. The results are demonstrated in FIGS. 20-21.

TABLE 3

| Sample | Starting Material (g) | Starting Material (Marrow-rich Bone)/Water (pre-warmed) | Rinse/Processing step number and incubation time | Total Volume (cc) |
|---|---|---|---|---|
| A | 12 | 1:5 incubated at 25° C. | 2x, 30 minutes each | 60 |
| B | | 1:6 incubated at 25° C. | | 72 |

Example 9

This Example evaluates an optional filtering step using different combinations of filters. Several combinations were attempted including stacking different sized filters, using wet or dry filters. Observations and time for filtering (or clogging) were obtained. Briefly, the soluble mem Tables 4-5 show the study design and observational results. The filtration solution starting volume ranged from about 96 to 176 cc. All solutions were prepared from one lot of marrow-rich bone. When BMP-2 was evaluated by ELISA in the resulting solutions, it was observed that BMP-2 was present at a higher concentration. The BMP-2 concentration was measured to be about 33.68 μg/cc starting marrow-rich bone.

TABLE 4

| Attempt # | Filter Type | Filter Size (μm) | Dry or Wet | Observations |
|---|---|---|---|---|
| 1 | Cellulose | 8 + 5 stacked | Wet | fast easy, 5-10 seconds |
| | Acetate | 3 + 1.2 stacked | | filtered in 1 min. 45 seconds, slowly |
| | | 0.8 | | fast, 20 seconds |
| | | 0.02 | Dry | fast, 20 seconds |
| 2 | Cellulose | 8, 5, 3 stacked | Dry | total volume in 2.5 min. |
| | Acetate | 0.8 + 1.2 stacked | | filtered in 1 min. 45 seconds, slowly |
| | | 1.2 | | filtered 110 mLs well in 30 seconds |
| | | 0.8 | | slower than day before, 6 min. |
| | | 0.2 (twice) | | Tried 2 of them, both clogged at 10 mLs |
| | PES | 0.45 | | meant to use 0.2, clogged at 20 mLs |
| | Cellulose | 0.8 | Wet | filtered in 20 seconds |
| | Acetate | 0.2 | Dry | clogged at 10 mLs |

TABLE 5

| Attempt # | Filter Type | Filter Size (μm) | Dry or Wet | Observations |
|---|---|---|---|---|
| 3 | Cellulose Acetate | 8 + 5 stacked | Wet | total volume in 3 min. 25 seconds *heard air leak in unit |
| | | 3 | | 20 seconds |
| | | 1.2 | | 55 seconds |
| | | 0.8 (twice) | | 120 mL in 7 min. and clogged, rest immediately (10-15 mL) |
| | | 0.2 | Dry | did not filter |
| | | 0.8 | Wet | 2 minutes |
| | | 0.8 | Wet | 35 seconds |
| | | 0.2 | Dry | 1/3 volume in 2 min, clogged |
| | | 0.2 | | little more than 1/3 in 3 minutes, clogged |
| | | 0.2 | | 45 sec to filter remaining |
| 4 | Cellulose Acetate | 8 + 5 + 3 stacked | Wet | didn't filter |
| | | 8 + 5 + 3 stacked | Dry | slow, 75-100 mLs in 2-3 min. |
| | | 8 + 5 | | filtered remainig volume easily |
| | | 3 | | 55 seconds |
| | | 1.2 | Wet | 85 seconds |
| | | 0.8 | | 30 seconds |
| | | 0.2 | Dry | well for 45 seconds, then last 5-10 mLs in 30 seconds |

Example 10

Figure 22:
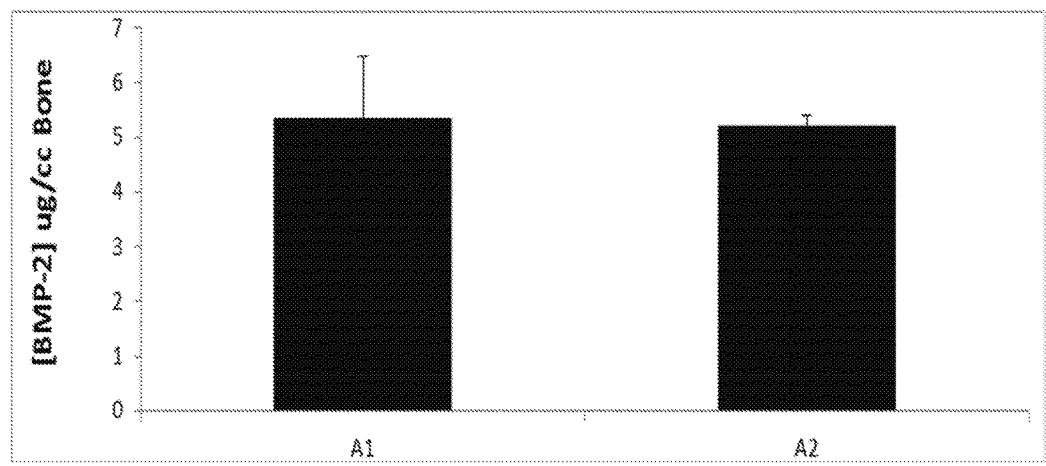
FIG. 22 shows a graph demonstrating BMP-2 content in duplicate preparations of a soluble bone marrow protein composition prepared using a using a high volume of processing solution (about 1000 mL).

This Example evaluated the effect of including an optional filtering step performed on a large volume (about 1250 cc) of starting volume of processing solution. About 225 g of bone marrow containing granules were processed in 1250 mL of water. The processing observations are shown in Table 6. As shown in FIG. 22, a considerable about of BMP-2 was present in the final soluble bone marrow protein composition and averaged about 5 μg/cc of starting bone marrow containing material.

TABLE 6

| Filter Size (μm) | Observations |
|---|---|
| 8 + 5 (Stacked) | Clogged @ 45 sec |
| | Clogged @ 45 sec |
| 8 | Slowed at 1 min, 180 mL in 2 min |
| | Slowed at 1 min, 120 mL in 2 min |
| | Sowed at 1 min, 140 mL in 2 min |
| | Slowed @ 1 min, 160 mL in 2 min |
| | Slowed @ 1 min, 150 mL in 1 min |
| | Filtered remaining in 40 sec. |
| 5 | Fast, easy, total volume in 40 sec. |
| 3 | Slowed at 5.5 min, filtered total in 7.5 min |
| 1.2 | Immediately slow, 80 mL in 1 min. |
| | Slowly, about 700 mL in 14 min. |
| 0.8 | 8 filters, each clogged around 2 min, each filtered around 130 mL |
| 0.2 | 6 filters total |

Example 11

This Example evaluates the effect of different stabilizer components and their effect on the binding of components of the soluble membrane protein composition to different graft scaffolds (e.g. VITOSS material, demineralized cortical bone, and mineralized cortical bone. The 1× stabilizer formulation contained (per 100 mL) 100 mg sucrose, 500 mg glycine, 370 mg glutamic acid, 2 mg NaCl, and 2 mg Polysorbate-80. Glutamic acid was varied in the stabilizer solution and was substituted in some instances with other mild acids such as acetic acid. The stabilizer component variations were as follows: (1) with glutamic acid 1×; (2) with glutamic acid 2.5×; (3) with glutamic acid 5×; (4) without glutamic acid but with 160 μL of 10% acetic acid; (5) without glutamic acid but with 320 μL of 10% acetic acid; (6) with glutamic acid 2.5×+160 μL of 10% acetic acid; (7) without glutamic acid but with 40 μL of 0.6N HCl; (8) without glutamic acid but with 80 μL of 0.6N HCl; and (9) with glutamic acid 2.5× and 40 μL of 0.6N HCl. Bound bioactive factors were indirectly determined by determining the amount of unbound bioactive factors remaining.

General processing parameters are shone in Table 7. Briefly, bone marrow containing starting material was weighed and processed in about 98 mLs of pre-warmed (37° C.) water for about 30 minutes. The solution was collected and fresh pre-warmed water was added to the bone marrow containing starting material and processed as before. The solution was collected and combined with the solution collected from the first step. The combined solution was stored at about 4° C. for about 2 hours. The chilled solution was cleaned by filtering and centrifugation as set forth in Table 7. 140 mLs was recovered after the cleaning filtration. The 140 mLs were divided into 9 aliquots and each aliquot was mixed with a different stabilizer from the stabilizer variations 1-9 previously described. Each of the 9 samples were then divided into 5 mL aliquots and frozen overnight at −80° C. Then, the samples were lyophilized.

Lyophilized samples from stabilizer variations 1, 3, 5, 6, 8, and 9 were reconstituted in 1 mL deionized water and duplicates were combined. 500 μL of the reconstituted sample was added to VITOSS material and incubated for about 15 minutes with no agitation at about 25° C. The liquid was collected and passed through a 100 μM nylon filter. This process was repeated using demineralized cortical bone or mineralized cortical bone instead of VITOSS material.

Figure 23:
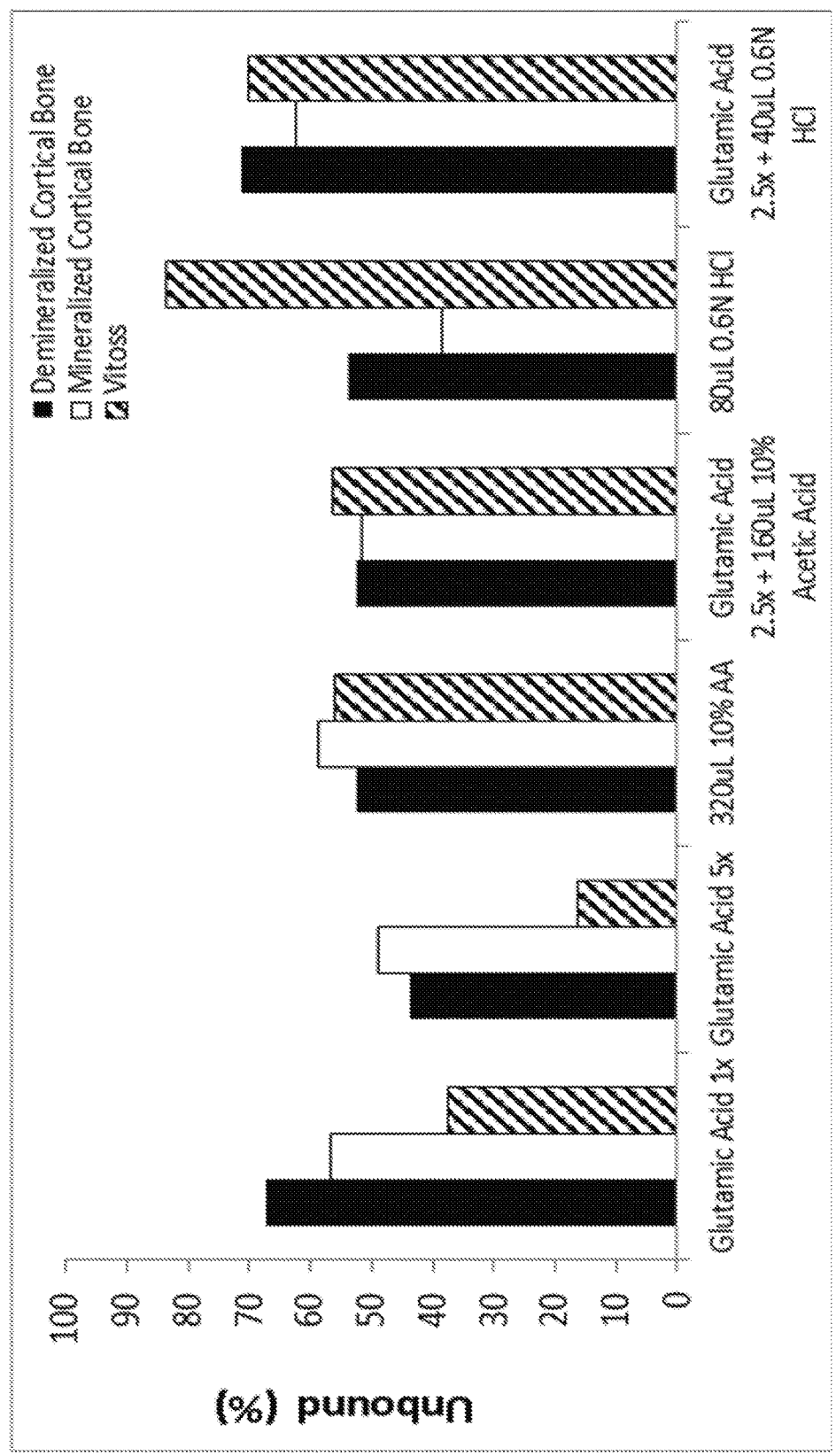
FIG. 23 shows a graph demonstrating the effect of a stabilizer component on binding to various graft scaffolds.

The reconstituted samples, the filtrate liquid, from all materials processed were lyophilized again and were incubated in 4M guanidine-HCl (Gu-HCl) pH 5.8 with shaking at 37° C. The amount of 4M Gu-HCl is based on the pre-lyophilized volume. The pH of the stabilizer solutions before and after reconstitution are shown in Table 8. For every 1 mL of sample volume, about 500 mL is used. Here the reconstituted samples prior to re-lyophilizing them ranged from about 140 μL to about 300 μL and the amount of 4M Gu-HCl was scaled to these amounts using the 1 mL:500 mL sample volume ratio. After incubating, samples were diluted 6× in 4M Gu-HCl pH 5.8 in duplicate and shaken at 25° C. for 1 hour. Samples were diluted 5×, 10×, and 25× in a calibrator diluent and tested for bioactive factors on Antigenix plates for evaluation of BMP-2 using ELISA. The % unbound BMP-2 is shown in FIG. 23.

Samples 1, 3, 5, 6, 8, and 9 were diluted in water at 1×, 10×, 25×, 50×, 100×, and 200× and total protein was evaluated using a BCA assay. The results of the total protein is not shown.

TABLE 7

| Donor | Sample | Granules (g) | Ratio w/pre-warmed H2O | Rinse | Extraction Filtration | Ctfg. | Cleaning Filtration | Stabilizer | Extraction |
|---|---|---|---|---|---|---|---|---|---|
| Lifelink - TNS-0202110001-15 | A | 39.26 | 1:5 shaken at 25 C. (196.30 mLs total) | 2x, 30 minutes each | 106, 75, 53 uM seives | 1000 g, 2 min. | 8, 5, 3, 1.2, 0.2 uM cellulose acetate | Sample mixed with stabilizer variations as described then lyophilized | 500 mL 4M Gu-HCl pH 5.8, 37 C., shaking, 24 hours |

TABLE 8

| Stabilizer Formulation | 0 (stabilizer without glutamic acid) | 1 | 2 | 3 | 4 | 5 | 6 | 7 | 8 | 9 |
|---|---|---|---|---|---|---|---|---|---|---|
| pH after preparing solution | 5.75 | 4.05 | 3.81 | 3.66 | 3.66 | 3.81 | 3.66 | 3.95 | 3.68 | 3.39 |
| pH after lyo'd and reconstituted In 1 mL | N/A | 4.5 | N/A | 4 | N/A | 4.5-5.0 | 4 | N/A | 7 | 4 |

We claim:

1. A method of making a soluble bone marrow protein composition, the method comprising:
   harvesting bone marrow from a cadaver donor to obtain harvested bone marrow, where the harvested bone marrow contains bone marrow cells;
   heating the harvested bone marrow to about 37° C. to about 60° C.;
   lysing one or more of the bone marrow cells to obtain a bone marrow cell lysate, wherein lysing is carried out at about 37° C. to about 60° C., wherein lysing is carried out in a solution selected from the group consisting of: water, acetic acid, hydrochloric acid, tricholoroacetic acid, hydrofluoric acid, hydrocyanic acid, hydrogen sulfide; and
   dehydrating at least a part of the bone marrow cell lysate to obtain a dehydrated soluble bone marrow protein composition.

2. The method of claim 1, further comprising the step of fractionating the bone marrow cell lysate via centrifugation to obtain a soluble bone marrow protein fraction after performing the step of lysing the bone marrow cells.

3. The method of claim 1, further comprising the step of washing the harvested bone marrow, wherein the step of washing occurs before the step of lysing.

4. The method of claim 1, further comprising the step of washing the harvested bone marrow, wherein the step of washing the harvested bone marrow occurs simultaneously with the step of lysing.

5. The method of claim 1, further comprising the step of adding a stabilization solution prior to the step of dehydrating.

6. The method of claim 1, further comprising the step of filtering the bone marrow cell lysate.

7. The method of claim 6, wherein filtering removes at least nucleic acids from the bone marrow cell lysate.

8. The method of claim 1, further comprising the step of selectively filtering the bone marrow cells to obtain a desired cell population prior to or during the step of lysing the bone marrow cells.

9. The method of claim 8, wherein the step of lysing further comprises lysing the desired cell population.

10. The method of claim 8, wherein the desired cell population is mesenchymal stem cells.

11. The method of claim 1, wherein an amount of the dehydrated soluble bone marrow protein composition is implanted in or otherwise administered to a subject in need thereof.

12. The method of claim 5, wherein an amount of the dehydrated soluble bone marrow protein composition in stabilization solution is implanted in or otherwise administered to a subject in need thereof.

13. The method of claim 1 further comprising applying an amount of the dehydrated soluble bone marrow protein composition to a scaffold.

14. The method of claim 13, wherein the scaffold is implanted in or otherwise administered to a subject in need thereof.

15. The method of claim 5, further comprising applying an amount of the dehydrated soluble bone marrow protein composition in stabilization solution to a scaffold.

16. The method of claim 15, wherein the scaffold is implanted in or otherwise administered to a subject in need thereof.

17. An implant comprising:
   a soluble bone marrow protein composition, wherein the soluble bone marrow composition is made by a method according to claim 1; and
   a non-bone scaffold, wherein one or more intracellular bioactive factors, cells, or one or more intracellular bioactive factors and cells of the soluble bone marrow protein composition are bound to the non-bone scaffold.

18. The implant of claim 17, wherein the bioactive factor is a protein selected from the group consisting of: a bone morphogenetic protein; epidermal growth factor, an insulin-like growth factor, a fibroblast growth factor, vascular endothelial growth factor, otseoprotegerin, and osteopontin.

19. The implant of claim 17, wherein the non-bone scaffold is a synthetic scaffold.

* * * * *